US011732269B2

(12) United States Patent
Kerstetter et al.

(10) Patent No.: US 11,732,269 B2
(45) Date of Patent: Aug. 22, 2023

(54) RECOMBINANT MAIZE B CHROMOSOME SEQUENCE AND USES THEREOF

(71) Applicant: MONSANTO TECHNOLOGY LLC, St. Louis, MO (US)

(72) Inventors: Randall Kerstetter, Wildwood, MO (US); Jonathan C. Lamb, Wildwood, MO (US); Thomas S. Ream, Wildwood, MO (US); Shiaw-Pyng Yang, St. Louis, MO (US); Xuefeng Zhou, St. Louis, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 1 day.

(21) Appl. No.: 15/765,049

(22) PCT Filed: Sep. 30, 2016

(86) PCT No.: PCT/US2016/054968
§ 371 (c)(1),
(2) Date: Mar. 30, 2018

(87) PCT Pub. No.: WO2017/059341
PCT Pub. Date: Apr. 6, 2017

(65) Prior Publication Data
US 2018/0273962 A1 Sep. 27, 2018

Related U.S. Application Data

(60) Provisional application No. 62/240,770, filed on Oct. 13, 2015, provisional application No. 62/237,048, filed on Oct. 5, 2015, provisional application No. 62/236,709, filed on Oct. 2, 2015.

(51) Int. Cl.
*C12N 15/82* (2006.01)
*C12Q 1/6895* (2018.01)
*C12N 15/64* (2006.01)

(52) U.S. Cl.
CPC ......... *C12N 15/8213* (2013.01); *C12N 15/64* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

| | | |
|---|---|---|
| 4,761,373 A | 8/1988 | Anderson et al. |
| 4,810,648 A | 3/1989 | Stalker |
| 5,013,659 A | 5/1991 | Bedbrook et al. |
| 5,015,580 A | 5/1991 | Christou et al. |
| 5,094,945 A | 3/1992 | Comai |
| 5,106,739 A | 4/1992 | Comai et al. |
| 5,141,870 A | 8/1992 | Bedbrook et al. |
| 5,159,135 A | 10/1992 | Umbeck |
| 5,188,958 A | 2/1993 | Moloney et al. |
| 5,217,902 A | 6/1993 | Jones et al. |
| 5,229,114 A | 7/1993 | Cregan et al. |
| 5,273,894 A | 12/1993 | Strauch et al. |
| 5,276,268 A | 1/1994 | Strauch et al. |
| 5,322,938 A | 6/1994 | McPherson et al. |
| 5,352,605 A | 10/1994 | Fraley et al. |
| 5,359,142 A | 10/1994 | McPherson et al. |
| 5,362,865 A | 11/1994 | Austin |
| 5,378,619 A | 1/1995 | Rogers |
| 5,378,824 A | 1/1995 | Bedbrook et al. |
| 5,463,174 A | 10/1995 | Moloney et al. |
| 5,463,175 A | 10/1995 | Barry et al. |
| 5,512,466 A | 4/1996 | Klee et al. |
| 5,530,196 A | 6/1996 | Fraley et al. |
| 5,538,880 A | 7/1996 | Lundquist et al. |
| 5,543,576 A | 8/1996 | van Ooijen et al. |
| 5,550,318 A | 8/1996 | Adams et al. |
| 5,561,236 A | 10/1996 | Leemans et al. |
| 5,589,610 A * | 12/1996 | De Beuckeleer .... C07K 14/415 435/320.1 |
| 5,591,616 A | 1/1997 | Hiei et al. |
| 5,605,011 A | 2/1997 | Bedbrook et al. |
| 5,608,149 A | 3/1997 | Barry et al. |
| 5,627,061 A | 5/1997 | Barry et al. |
| 5,633,435 A | 5/1997 | Barry et al. |
| 5,633,437 A | 5/1997 | Bernasconi et al. |
| 5,637,489 A | 6/1997 | Strauch et al. |
| 5,641,876 A | 6/1997 | McElroy et al. |
| 5,646,024 A | 7/1997 | Leemans et al. |
| 5,659,122 A | 8/1997 | Austin |
| 5,689,041 A | 11/1997 | Mariani et al. |
| 5,731,179 A | 3/1998 | Komari et al. |
| 5,750,871 A | 5/1998 | Moloney et al. |
| 5,750,876 A | 5/1998 | Barry et al. |

(Continued)

FOREIGN PATENT DOCUMENTS

| | | |
|---|---|---|
| CN | 101484581 A | 7/2009 |
| CN | 103289959 A | 9/2013 |

(Continued)

OTHER PUBLICATIONS

Tröster et al. (1989) Mol Gen Genet 217:533-35.*
Lamperti et al. (1992) Nucl Acids Res 20(11):2741-4.*
Vainstein et al. (2011) Trends Biotech 29(8):363-69.*
Svitashev et al. (2002) Plant J 32:433-45.*
Naito et al. (2015) Bioinformatics 31:1120-23.*
AY426742 1 NCBI (2004).*
NCBI Blast Align (2020) Seq ID No. 158.pdf.*
U.S. Appl. No. 62/375,618, filed Aug. 16, 2016, Caldo et al.
Beurdeley et al., "Compact designer TALENs for efficient genome engineering," *Nature Communications*, 4:1762, 8 pages (2013).
Bevan et al., "Structure and transcription of the nopaline synthase gene region of T-DNA," *Nucleic Acids Research*, 11(2):369-385 (1983).

(Continued)

*Primary Examiner* — Russell T Boggs
(74) *Attorney, Agent, or Firm* — Morrison & Foerster LLP

(57) ABSTRACT

The present disclosure provides maize B chromosome genomic loci and methods of using for agronomic practices.

16 Claims, 2 Drawing Sheets
Specification includes a Sequence Listing.

(56) References Cited

U.S. PATENT DOCUMENTS

| | | | |
|---|---|---|---|
| 5,767,366 A | 6/1998 | Sathasivan et al. | |
| 5,824,877 A | 10/1998 | Hinchee et al. | |
| 5,837,848 A | 11/1998 | Ely et al. | |
| 5,850,019 A | 12/1998 | Maiti et al. | |
| 5,869,720 A | 2/1999 | John | |
| 5,914,451 A | 6/1999 | Martinell et al. | |
| 5,958,745 A | 9/1999 | Gruys et al. | |
| 5,981,834 A | 11/1999 | John et al. | |
| 5,985,605 A | 11/1999 | Cheng et al. | |
| 5,998,700 A | 12/1999 | Lightfoot et al. | |
| 6,002,070 A | 12/1999 | D'Halluin et al. | |
| 6,011,199 A | 1/2000 | Speirs et al. | |
| 6,040,497 A | 3/2000 | Spencer et al. | |
| 6,051,753 A | 4/2000 | Comai et al. | |
| 6,051,756 A | 4/2000 | Chen et al. | |
| 6,072,103 A | 6/2000 | Wu et al. | |
| 6,080,560 A | 6/2000 | Russell et al. | |
| 6,140,075 A | 10/2000 | Russell et al. | |
| 6,140,078 A | 10/2000 | Sanders et al. | |
| 6,153,812 A | 11/2000 | Fry et al. | |
| 6,160,208 A | 12/2000 | Lundquist et al. | |
| 6,166,292 A | 12/2000 | Osumi et al. | |
| 6,171,640 B1 | 1/2001 | Bringe | |
| 6,175,060 B1 | 1/2001 | Lefebvre et al. | |
| 6,177,611 B1 | 1/2001 | Rice | |
| 6,225,105 B1 | 5/2001 | Sathasivan et al. | |
| 6,228,623 B1 | 5/2001 | Asrar et al. | |
| 6,232,526 B1 | 5/2001 | McElroy et al. | |
| 6,252,138 B1 | 6/2001 | Karimi et al. | |
| 6,265,638 B1 | 7/2001 | Bidney et al. | |
| 6,271,443 B1 | 8/2001 | Stalker et al. | |
| 6,294,714 B1 | 9/2001 | Matsunaga et al. | |
| 6,297,056 B1 | 10/2001 | Tulsieram et al. | |
| RE37,543 E | 2/2002 | Kruger et al. | |
| 6,380,462 B1 | 4/2002 | Kridl | |
| 6,384,301 B1 | 5/2002 | Martinell et al. | |
| 6,399,861 B1 | 6/2002 | Anderson et al. | |
| 6,414,222 B1 | 7/2002 | Gengenbach et al. | |
| 6,426,446 B1 | 7/2002 | McElroy et al. | |
| 6,426,447 B1 | 7/2002 | Knauf et al. | |
| 6,429,357 B1 | 8/2002 | McElroy et al. | |
| 6,429,362 B1 | 8/2002 | Crane | |
| 6,433,252 B1 | 8/2002 | Kriz et al. | |
| 6,437,217 B1 | 8/2002 | McElroy et al. | |
| 6,444,876 B1 | 9/2002 | Lassner et al. | |
| 6,459,018 B1 | 10/2002 | Knutzon | |
| 6,476,295 B2 | 11/2002 | Barry et al. | |
| 6,483,008 B1 | 11/2002 | Dehesh et al. | |
| 6,489,461 B1 | 12/2002 | Dehesh et al. | |
| 6,495,739 B1 | 12/2002 | Lassner et al. | |
| 6,531,648 B1 | 3/2003 | Lanahan et al. | |
| 6,537,750 B1 | 3/2003 | Shorrosh | |
| 6,538,178 B1 | 3/2003 | Kishore | |
| 6,538,179 B1 | 3/2003 | Barry et al. | |
| 6,538,181 B1 | 3/2003 | Stalker et al. | |
| 6,541,259 B1 | 4/2003 | Lassner et al. | |
| 6,576,818 B1 | 6/2003 | Stalker et al. | |
| 6,589,767 B1 | 7/2003 | Knutzon et al. | |
| 6,596,538 B1 | 7/2003 | Lardizabal et al. | |
| 6,613,963 B1 | 9/2003 | Gingera et al. | |
| 6,635,806 B1 | 10/2003 | Kriz et al. | |
| 6,653,530 B1 | 11/2003 | Shewmaker et al. | |
| 6,660,849 B1 | 12/2003 | Dehesh | |
| 6,706,950 B2 | 3/2004 | Dehesh | |
| 6,723,837 B1 | 4/2004 | Karunanandaa et al. | |
| 6,770,465 B1 | 8/2004 | Dehesh et al. | |
| 6,774,283 B1 | 8/2004 | Goodman et al. | |
| 6,812,379 B2 | 11/2004 | Staub | |
| 6,822,141 B2 | 11/2004 | Lardizabal et al. | |
| 6,828,475 B1 | 12/2004 | Metz et al. | |
| 7,122,722 B2 | 10/2006 | Trolinder et al. | |
| 2003/0028917 A1 | 2/2003 | Gruys et al. | |
| 2003/0083480 A1 | 5/2003 | Castle et al. | |
| 2003/0110532 A1 | 6/2003 | ArmoStrong et al. | |
| 2003/0115626 A1 | 6/2003 | Weeks et al. | |
| 2003/0135879 A1 | 7/2003 | Weeks et al. | |
| 2004/0123342 A1 | 6/2004 | Elliott et al. | |
| 2004/0177399 A1 | 9/2004 | Hammer et al. | |
| 2004/0216189 A1 | 10/2004 | Houmard et al. | |
| 2004/0237142 A1 | 11/2004 | Gilbertson et al. | |
| 2005/0183170 A1 | 8/2005 | Fillatti et al. | |
| 2014/0283166 A1* | 9/2014 | Chomet et al. | C12N 15/8213 536/23.6 |
| 2015/0059010 A1* | 2/2015 | Cigan et al. | A01H 5/00 800/298 |
| 2015/0167010 A1 | 6/2015 | Lamb et al. | |

FOREIGN PATENT DOCUMENTS

| | | |
|---|---|---|
| EP | 0 275 957 | 7/1988 |
| EP | 0 385 962 A1 | 9/1990 |
| WO | WO 87/04181 | 7/1987 |
| WO | WO 89/00193 | 1/1989 |
| WO | WO 99/27116 | 6/1999 |
| WO | WO 2004/009761 A2 | 1/2004 |
| WO | WO 2004/074443 A2 | 9/2004 |
| WO | WO 2005/003362 A2 | 1/2005 |
| WO | WO 2007/134122 A2 | 11/2007 |
| WO | 2017059341 A1 | 4/2017 |

OTHER PUBLICATIONS

Callis et al., "Heat Inducible Expression of a Chimeric Maize hsp70CAT Gene in Maize Protoplasts," *Plant Physiol*, 88:965-968 (1988).

Carrington and Freed, "Cap-independent enhancement of translation by a plant polyvirus 5'nontranslated region," *Journal of Virology*, 64: 1590-1597 (1990).

Castle et al., "Discovery and directed evolution of a glyphosate tolerance gene," *Science*, 304: 1151-1154 (2004).

Cermak et al., "Efficient design and assembly of custom TALEN and other TAL effector-based constructs for DNA targeting," *Nucleic Acids Res.*, 39(12):e82, 11 pages (2011).

Chandler et al. "Two Regulatory Genes of the Maize Anthocyanin Pathway Are Homologous: Isolation of B Utilizing R Genomic Sequences," *The Plant Cell*, 1(12):1175-1183 (1989).

Cheng et al., "Evolution of the heterochromatic regions on maize B long arm based on the sequence structure of CL-repeat variants," *Chromosome Research*, 18:605-619 (2010).

Comeau et al., "Media for the in ovulo culture of proembryos of wheat and wheat-derived interspecific hybrids or haploids," *Plant Science*, 81(1):117-125 (1992).

Dekeyser et al., "Evaluation of selectable markers for rice transformation," *Plant Physiology*, 90: 217-223 (1989).

Della-Cioppa et al, "Translocation of the precursor of 5-enolpyruvylshikimate-3-phosphate synthase into chloroplasts of higher plants in vitro," *PNAS USA*. 83:6873-6877, (1986).

Depicker et al., "Nopaline synthase: transcript mapping and DNA sequence," *Journal of Molecular and Applied Genetics*, 1(6):561-573 (1982).

Doyle et al., "TAL Effector-Nucleotide Targeter (TALE-NT) 2.0: tools for TAL effector design and target prediction," *Nucleic Acids Res.*, 40(W1):W117-W122 (2012).

Ebert et al, "Identification of an essential upstream element in the nopaline synthase promoter by stable and transient assays," *PNAS USA*, 84:5745-5749 (1987).

Extended European Search Report dated Apr. 29, 2019, in European Patent Application No. 16852769.5.

Fraley et al., "Expression of bacterial genes in plant cells," *PNAS USA*, 80:4803-4807 (1983).

Gabsalilow et al., "Site- and strand-specific nicking of DNA by fusion proteins derived from MutH and I-SceI or TALE repeats," *Nucleaic Acids Research*, 41:e83, 11 pages (2013).

Gaeta et al., "Synthetic chromosome platforms in plants," *Annual Review of Plant Biology*, 63:307-330 (2012).

Gao et al., "DNA-guided genome editing using the *Natronobacterium gregoryi* Argonaute," *Nature Biotechnology*, 34:768-773 (2016).

GenBank Accession V00087.

(56) References Cited

OTHER PUBLICATIONS

Huang et al., "Application of a superword array in genome assembly," *Nucleic Acids Research*, 34.1: 201-205 (2006).
Hui, et al., "Strategies for cloning unknown cellular flanking DNA sequences from foreign integrants," *Cellular and Molecular Life Sciences CMLS*, 54(12):1403-1411 (1998).
Kato et al., "Chromosome Painting for Plant Biotechnology," *Plant Chromosome Engineering in Methods in Molecular Biology*, Humana Press, Totowa, NJ:67-96 (2011).
Kelliher at al., "Maternal Haploids Are Preferentially Induced by CENH3-tailswap Transgenic Complementation in Maize," *Frontiers in Plant Science*, 7:414 (2016).
Koo et al., "Distinct DNA methylation patterns associated with active and inactive centromeres of the maize B chromosome," *Genome Research*, 21(6):908-914 (2011).
Kuhlemeier et al., "The Pea rbcS-3A Promoter Mediates Light Responsiveness but Not Organ Specificity," *The Plant Cell*, 1(4):471-478 (1989).
Lamb et al., "Localization and transcription of a retrotransposon-derived element on the maize B chromosome," *Chromosome Research*, 15:383-398 (2007).
Lawton et al., "Expression of a soybean β-conclycinin gene under the control of the Cauliflower Mosaic $_{35}$S and $_{19}$S promoters in transformed petunia tissues," *Plant Molecular Biology*, 9(4):315-324 (1987).
Marcotte et al., "Abscisic Acid-Responsive Sequences from the Em Gene of Wheat," *The Plant Cell*, 1:969-976 (1989).
Odell et al., "Identification of DNA sequences required for activity of the cauliflower mosaic virus 35S promoter," *Nature*, 313:810-812 (1985).
Partial Supplementary European Search Report dated Jan. 30, 2019, in European Patent Application No. 16852769.5.
Schnable et al., "The B73 maize genome: complexity, diversity, and dynamics," *Science*, 326:1112-5 (2009).
Schnäffner et al., "Maize rbcS Promoter Activity Depends on Sequence Elements Not Found in Dicot rbcS Promoters," *The Plant Cell*, 3:997-1012 (1991).

Siebertz et al., "cis-Analysis of the Wound-Inducible Promoter wun1 in Transgenic Tobacco Plants and Histochemical Localization of Its Expression," *The Plant Cell*, 1:961-968 (1989).
Tonooka and Fujishima, "Comparison and critical evaluation of PCR-mediated methods to walk along the sequence of genomic DNA," *Applied Microbiology and Biotechnology*, 85.1: 37 (2009).
Yang et al., "Maize sucrose synthase-1 promoter directs phloem cell-specific expression of *Gus* gene in transgenic tobacco plants," *PNAS*, 8(11):4144-4148 (1990).
Yanik et al., "TALE-PvuII Fusion Proteins—Novel Tools for Gene Targeting," *PLoS One*. 8:e82539, 13 pages (2013).
Yu et al., "Construction and behavior of engineered mimichromosomes in maize," PNAS 104(21):8924-8929 2007.
EMBL-EBI sequence AE016822.1 (Aug. 5, 2004) nucleotides 400648-400794.
International Search Report dated Feb. 23, 2017 in International Application No. PCT/US2016/054968.
Frame et al., "Improved Agrobacterium-mediated transformation of three maize inbred lines using MS salts," Plant Cell Rep, 25:1024-1034 (2006).
Gao et al., "Complex Trait Loci in Maize Enabled by CRISPR-Cas9 Mediated Gene Insertion," *Front. Plant Sci.*, 11:535 (2020).
Kuscu et al., "Genome-wide analysis reveals characteristics of off-target sites bound by the Cas9 endonuclease," *Nature Biotechnology*, 32:677-683 (2014).
Takano et al., "The structures of integration sites in transgenic rice," Plant J., 11:353-361 (1997).
Cheng et al., "Cloning and Characterization of Maize B Chromosome Sequences Derived From Microdissection," *Genetics*, 299-310 (2003).
Blavet, N. et al. (Jun. 4, 2021). "Sequence of the Supernumerary B Chromosome of Maize Provides Insight into its Drive Mechanism and Evolution," PNAS 118(23):e2104254118, 11 pages.
Yu, W. et al. (Nov. 14, 2006). "Telomere-Mediated Chromosomal Truncation in Maize," PNAS 103(46):17331-17336.

* cited by examiner

RECOMBINANT MAIZE B CHROMOSOME SEQUENCE AND USES THEREOF

CROSS-REFERENCE TO RELATED APPLICATIONS AND INCORPORATION OF SEQUENCE LISTING

This application is a U.S. National Stage Application of International Application No. PCT/US2016/054968 filed Sep. 30, 2016, which claims the benefit of U.S. Provisional Patent Application No. 62/236,709 filed Oct. 2, 2015, U.S. Provisional Patent Application No. 62/237,048 filed Oct. 5, 2015, and U.S. Provisional Patent Application No. 62/240,770 filed Oct. 13, 2015, which are incorporated by reference in their entirety herein. The sequence listings contained in the files "P34350US00_SEQ.text" (3,202,544 bytes (measured in operating system MS Windows) created on Oct. 2, 2015, filed with U.S. Provisional Patent Application No. 62/236,709 on Oct. 2, 2015), "P34350US01_SEQ.txt" (3,202,584 bytes (measured in operating system MS Windows) created on Oct. 5, 2015, filed with U.S. Provisional Patent Application No. 62/237,048 on Oct. 5, 2015) and "P34350US02_SEQ.txt" (3,655,665 bytes (measured in operating system MS Windows) created on Oct. 13, 2015, filed with U.S. Provisional Patent Application No. 62/240,770 on Oct. 13, 2015) are incorporated by reference in their entirety herein. A computer readable form of a sequence listing is filed with this application by electronic submission and is incorporated into this application by reference in its entirety. The sequence listing is contained in the file named Sequence Listing-P34350US03.txt, which is 3,640,457 bytes in size (measured in operating system MS Windows) and was created on Mar. 29, 2018.

BACKGROUND

B chromosomes are supernumerary chromosomes that occur in many organisms and differ from the standard nuclear chromosomes (A chromosomes) in that they rarely carry active genes. These chromosomes are not essential for the life of a species.

The first transgenic plants were generated in the 1990s and were the result of random insertion of transgene DNA into nuclear A chromosomes (e.g., Roundup Ready® soybean). As more transgenic events conferring separate traits (e.g., insect resistance, drought tolerance, herbicide tolerance, quality traits) have been generated, there is a desire of plant breeders and farmers to have multiple traits in the crop plant. As the number of traits per plant increases, there is a corresponding increase in the resources and technical challenges needed to generate a breeding stack of multiple traits present on A chromosomes in elite germplasm. Additionally, with increased traits there exists a risk of linkage drag. In maize, trait stacking and reduction of the risk of A chromosome linkage drag may be solved by developing the next generation of transgenic traits on the B chromosome.

SUMMARY

Figure 1:
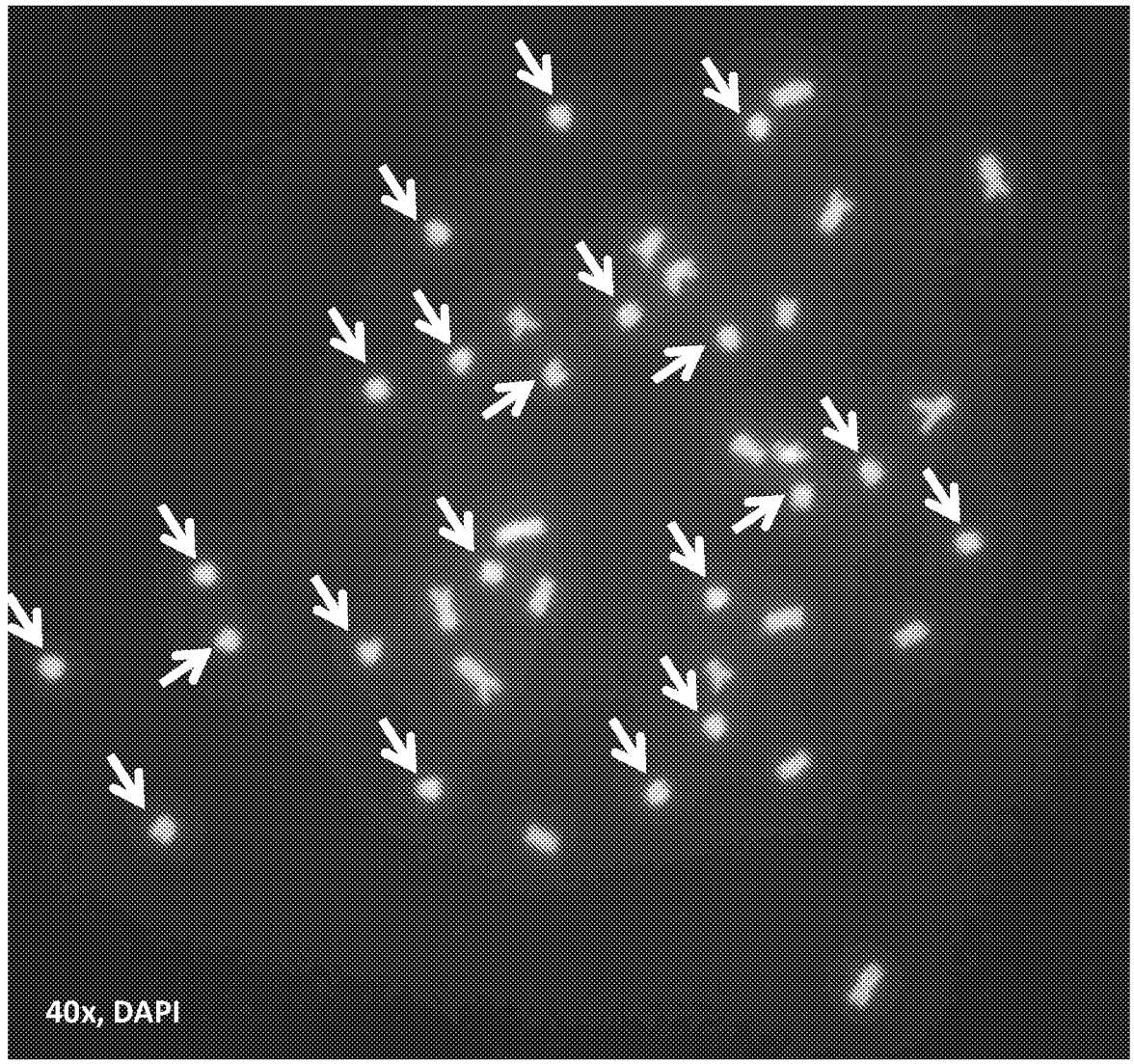
FIG. 1. Image of a maize root tip cell with the chromosomes stained with DAPI fluorescence stain. The arrows show the 20 B chromosomes in the nucleus of the cell from an individual plant. Magnification of the image is 40×.

Several embodiments relate to a recombinant nucleic acid comprising: a nucleic acid sequence of having at least 90%, at least 91%, at least 92%, at least 93%, 94%, at least 95%, at least 96%, at least 97%, at least 98%, at least 99%, or 100%, sequence identity to at least 0.25 Kb, 0.5 Kb, 0.75 Kb, 1 Kb, 1.25 Kb, 1.5 Kb, 1.75 Kb, 2 Kb, 2.25 Kb, 2.5 Kb, 2.75 Kb, 3 Kb, 3.25 Kb, 3.5 Kb, 3.75 Kb, 4 Kb, 4.25 Kb, 4.5 Kb, 4.75 Kb, or 5 Kb of a maize B chromosome sequence selected from the group consisting of SEQ ID NOs: 10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888, and at least one DNA of interest, wherein at least one of the DNA of interest is integrated into the maize B chromosome sequence to produce the recombinant nucleic acid. In some embodiments, the DNA of interest is integrated at double-strand break generated by one or more site-specific genome modification enzymes. In some embodiments, the DNA of interest encodes site-specific genome modification enzyme. In some embodiments, the DNA of interest encodes one or more of an endonuclease, a recombinase, a transposase, a helicase or any combination thereof. In some embodiments, the DNA of interest comprises one or more gene expression cassettes, wherein the gene expression cassettes are selected from the group comprising: an insecticidal resistance gene expression cassette, herbicide tolerance gene expression cassette, nitrogen use efficiency gene expression cassette, a water use efficiency gene expression cassette, a nutritional quality gene expression cassette, a DNA binding gene expression cassette, a selectable marker gene expression cassette, an RNAi construct expression cassette, a site-specific genome modification enzyme gene expression cassette, or an expression cassette encoding one or more of a CRIPR associate protein, a tracr RNA and a guide RNA.

Several embodiments relate to a maize plant comprising a recombinant nucleic acid comprising: a nucleic acid sequence of having at least 90%, at least 91%, at least 92%, at least 93%, 94%, at least 95%, at least 96%, at least 97%, at least 98%, at least 99%, or 100%, sequence identity to at least 0.25 Kb, 0.5 Kb, 0.75 Kb, 1 Kb, 1.25 Kb, 1.5 Kb, 1.75 Kb, 2 Kb, 2.25 Kb, 2.5 Kb, 2.75 Kb, 3 Kb, 3.25 Kb, 3.5 Kb, 3.75 Kb, 4 Kb, 4.25 Kb, 4.5 Kb, 4.75 Kb, or 5 Kb of a maize B chromosome sequence selected from the group consisting of SEQ ID NOs: 10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888, and at least one DNA of interest, wherein at least one of the DNA of interest is integrated into the maize B chromosome sequence to produce the recombinant nucleic acid. In some embodiments, the DNA of interest is integrated at double-strand break generated by one or more site-specific genome modification enzymes. In some embodiments, the DNA of interest encodes site-specific genome modification enzyme. In some embodiments, the DNA of interest encodes one or more of an endonuclease, a recombinase, a transposase, a helicase or any combination thereof. In some embodiments, the DNA of interest comprises one or more gene expression cassettes, wherein the gene expression cassettes are selected from the group comprising: an insecticidal resistance gene expression cassette, herbicide tolerance gene expression cassette, nitrogen use efficiency gene expression cassette, a water use efficiency gene expression cassette, a nutritional quality gene expression cassette, a DNA binding gene expression cassette, a selectable marker gene expression cassette, an RNAi construct expression cassette, a site-specific genome modification enzyme gene expression cassette, or an expression cassette encoding one or more of a CRIPR associate protein, a tracr RNA and a guide RNA.

Several embodiments relate to a recombinant B chromosome comprising: a nucleic acid sequence of having at least 90%, at least 91%, at least 92%, at least 93%, 94%, at least 95%, at least 96%, at least 97%, at least 98%, at least 99%, or 100%, sequence identity to at least 0.25 Kb, 0.5 Kb, 0.75 Kb, 1 Kb, 1.25 Kb, 1.5 Kb, 1.75 Kb, 2 Kb, 2.25 Kb, 2.5 Kb, 2.75 Kb, 3 Kb, 3.25 Kb, 3.5 Kb, 3.75 Kb, 4 Kb, 4.25 Kb, 4.5 Kb, 4.75 Kb, or 5 Kb of a maize B chromosome sequence selected from the group consisting of SEQ ID NOs: 10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888, and at least one DNA of interest, wherein at least one of the DNA of interest is integrated into the maize B chromosome sequence to produce the recombinant nucleic acid. In some embodiments, the DNA of interest is integrated at double-strand break generated by one or more site-specific genome modification enzymes. In some embodiments, the DNA of interest encodes site-specific genome modification enzyme. In some embodiments, the DNA of interest encodes one or more of an endonuclease, a recombinase, a transposase, a helicase or any combination thereof. In some embodiments, the DNA of interest comprises one or more gene expression cassettes, wherein the gene expression cassettes are selected from the group comprising: an insecticidal resistance gene expression cassette, herbicide tolerance gene expression cassette, nitrogen use efficiency gene expression cassette, a water use efficiency gene expression cassette, a nutritional quality gene expression cassette, a DNA binding gene expression cassette, a selectable marker gene expression cassette, an RNAi construct expression cassette, a site-specific genome modification enzyme gene expression cassette, or an expression cassette encoding one or more of a CRIPR associate protein, a tracr RNA and a guide RNA.

Several embodiments relate to a method of making a maize cell comprising at least one DNA of interest integrated in a B chromosome by selecting at least one target having at least 90%, at least 91%, at least 92%, at least 93%, 94%, at least 95%, at least 96%, at least 97%, at least 98%, at least 99%, or 100%, sequence identity to at least 0.25 Kb, 0.5 Kb, 0.75 Kb, 1 Kb, 1.25 Kb, 1.5 Kb, 1.75 Kb, 2 Kb, 2.25 Kb, 2.5 Kb, 2.75 Kb, 3 Kb, 3.25 Kb, 3.5 Kb, 3.75 Kb, 4 Kb, 4.25 Kb, 4.5 Kb, 4.75 Kb, or 5 Kb of a maize B chromosome sequence selected from the group consisting of SEQ ID NOs: 10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-

717, 719-729, 731-734, 736-738, 740, 741, 743-748, 750, 752-764, 766, 767, 770, 771, 773, 774, 776-785, 787-791, and 793-888; selecting a site specific genome modification enzyme that specifically cleaves the target site; introducing the site specific genome modification enzyme into the maize cell; introducing the DNA of interest into the maize cell; integrating the DNA of interest into the target site; and selecting a transgenic maize cell comprising the at least one of the DNA of interest integrated into the B chromosome. In some embodiments, the DNA of interest is integrated at double-strand break generated by one or more site-specific genome modification enzymes. In some embodiments, the DNA of interest encodes site-specific genome modification enzyme. In some embodiments, the DNA of interest encodes one or more of an endonuclease, a recombinase, a transposase, a helicase or any combination thereof. In some embodiments, the DNA of interest comprises one or more gene expression cassettes, wherein the gene expression cassettes are selected from the group comprising: an insecticidal resistance gene expression cassette, herbicide tolerance gene expression cassette, nitrogen use efficiency gene expression cassette, a water use efficiency gene expression cassette, a nutritional quality gene expression cassette, a DNA binding gene expression cassette, a selectable marker gene expression cassette, an RNAi construct expression cassette, a site-specific genome modification enzyme gene expression cassette, or an expression cassette encoding one or more of a CRIPR associate protein, a tracr RNA and a guide RNA.

Several embodiments relate to a method of providing a site specific genome modification enzyme to a maize cell comprising integrating at least one site specific genome modification enzyme into a sequence having at least 90%, at least 91%, at least 92%, at least 93%, 94%, at least 95%, at least 96%, at least 97%, at least 98%, at least 99%, or 100%, sequence identity to at least 0.25 Kb, 0.5 Kb, 0.75 Kb, 1 Kb, 1.25 Kb, 1.5 Kb, 1.75 Kb, 2 Kb, 2.25 Kb, 2.5 Kb, 2.75 Kb, 3 Kb, 3.25 Kb, 3.5 Kb, 3.75 Kb, 4 Kb, 4.25 Kb, 4.5 Kb, 4.75 Kb, or 5 Kb of a maize B chromosome sequence selected from the group consisting of SEQ ID NOs: 10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888; and selecting a maize cell comprising site specific genome modification enzyme integrated into the B chromosome. In some embodiments, the site-specific genome modification enzyme specifically cleaves a target site in one or more A Chromosomes into which a DNA of interest is integrated. In some embodiments, the DNA of interest comprises one or more gene expression cassettes, wherein the gene expression cassettes are selected from the group comprising: an insecticidal resistance gene expression cassette, herbicide tolerance gene expression cassette, nitrogen use efficiency gene expression cassette, a water use efficiency gene expression cassette, a nutritional quality gene expression cassette, a DNA binding gene expression cassette, a selectable marker gene expression cassette, and an RNAi construct expression cassette. In some embodiments, progeny are selected that comprise the DNA of interest but do not comprise the B chromosome comprising the site specific genome modification enzyme. In some embodiments, the B chromosome comprises a negative selection marker.

Several embodiments relate to a recombinant nucleic acid comprising a nucleic acid sequence of at least 1 Kb having at least 90% sequence identity with a maize B chromosome sequence selected from the group consisting of SEQ ID NOs: 10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888, and a DNA of interest integrated into the maize B chromosome sequence to produce the recombinant nucleic acid. In some embodiments, the recombinant nucleic acid comprises a DNA of interest that is integrated proximal to a target site for a site-specific genome modification enzyme. In some embodiments, the site-specific genome modification enzyme is an endonuclease. In some embodiments, the site-specific genome modification enzyme is a recombinase. In some embodiments, the site-specific genome modification enzyme is a transposase. In some embodiments, the site-specific genome modification enzyme is a helicase. In some embodiments, the site-specific genome modification enzyme is any combination of an endonuclease, a recombinase, a transposase and a helicase. In some embodiments, the target site is specific for maize B chromosome sequence. In a further embodiment, the target site is specific for maize B chromosome sequence is selected from one or more of the group comprising SEQ ID NOs: 10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888. In some embodiments, the site-specific genome modification enzyme is an endonuclease selected from a meganuclease, a zinc finger nuclease, a transcription activator-like effector nuclease (TALEN), an Argonaute, a DNA-guided recombinase, a DNA-guided endonuclease, an RNA-guided recombinase, an RNA-guided endonuclease, a type I CRISPR-Cas system, type II CRISPR-Cas system and a type III CRISPR-Cas system. In some embodiments, the endonuclease is selected from the group comprising Cpf1, Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4 nuclease. In some embodiments, the site-specific genome modification enzyme is an RNA-guided recombinase. In some embodiments, the site-specific genome modification enzyme is a fusion protein comprising a recombinase and a CRISPR associated protein. In some embodiments, the recombinase is a tyrosine recombinase attached to a DNA recognition motif, or a serine recombinase attached to a DNA recognition motif. In some embodiments, the recombinase is a Cre recombinase, a Flp recombinase, and a Tnp1 recombinase, a PhiC31 integrase, an R4 integrase, or a TP-901 integrase. In some embodiments, transposase is a DNA transposase attached to a DNA binding domain. In some embodiments, the DNA of interest does not encode a peptide. In some embodiments, the DNA of interest does encode a peptide. In some embodiments, the DNA of interest comprises one or more gene expression cassettes. In some embodiments, the gene expression cassette is selected from the group comprising an insecticidal resistance gene expression cassette, an herbicide tolerance gene expression cassette, a nitrogen use efficiency gene expression cassette, a water use efficiency gene expression cassette, a nutritional quality gene expression cassette, a DNA binding gene expression cassette, a selectable marker gene expression cassette, an RNAi construct expression cassette, a site-specific genome modification enzyme gene expression cassette, an expression cassette encoding a recombinant guide RNA of an RNA-guided endonuclease, or an expression cassette encoding a recombinant DNA guide. In some embodiments, the DNA of interest is integrated into the target site of the maize B chromosome via a homology directed repair integration method. In some embodiments, the DNA of interest is integrated into the target site of the maize B chromosome via a non-homologous end joining integration method. In some embodiments, the DNA of interest and/or the maize B chromosome target site sequences are modified during integration of the DNA of interest into the target site of the maize B chromosome sequence. In some embodiments, the recombinant nucleic acid is present in a maize plant, a maize plant part, a maize seed, or a maize plant cell.

Several embodiments relate to a recombinant nucleic acid comprising a nucleic acid sequence of at least 1 Kb having at least 90% sequence identity with a maize B chromosome sequence selected from the group consisting of SEQ ID NOs: 10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888, and a DNA of interest integrated into the maize B chromosome sequence to produce the recombinant nucleic acid. In some embodiments, the recombinant nucleic acid comprises a DNA of interest integrated between a pair of target sites for a site-specific genome modification enzyme. In some embodiments, the site-specific genome modification enzyme is an endonuclease. In some embodiments, the site-specific genome modification enzyme is a recombinase. In some embodiments, the site-specific genome modification enzyme is a transposase. In some embodiments, the site-specific genome modification enzyme is a helicase. In some embodiments, the site-specific genome modification enzyme is any combination of an endonuclease, a recombinase, a transposase and a helicase. In some embodiments, the target site is specific for maize B chromosome sequence. In a further embodiment, the target site is specific for maize B chromosome sequence is selected from one or more of the group comprising SEQ ID NOs: 10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888. In some embodiments, the site-specific genome modification enzyme is an endonuclease selected from a meganuclease, a zinc finger nuclease, a transcription activator-like effector nuclease (TALEN), an Argonaute, a DNA-guided recombinase, a DNA-guided endonuclease, an RNA-guided recombinase, an RNA-guided endonuclease, a type I CRISPR-Cas system, type II CRISPR-Cas system and a type III CRISPR-Cas system. In some embodiments, the endonuclease is selected from the group comprising Cpf1, Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4 nuclease. In some embodiments, the site-specific genome modification enzyme is an RNA-guided recombinase. In some embodiments, the site-specific genome modification enzyme is a fusion protein comprising a recombinase and a CRISPR associated protein. In some embodiments, the recombinase is a tyrosine recombinase attached to a DNA recognition motif, or a serine recombinase attached to a DNA recognition motif. In some embodiments, the recombinase is a Cre recombinase, a Flp recombinase, and a Tnp1 recombinase, a PhiC31 integrase, an R4 integrase, or a TP-901 integrase. In some embodiments, transposase is a DNA transposase attached to a DNA binding domain. In some embodiments, the DNA of interest does not encode a peptide. In some embodiments, the DNA of interest does encode a peptide. In some embodiments, the DNA of interest comprises one or more gene expression cassettes. In some embodiments, the gene expression cassette is selected from the group comprising an insecticidal resistance gene expression cassette, an herbicide tolerance gene expression cassette, a nitrogen use efficiency gene expression cassette, a water use efficiency gene expression cassette, a nutritional quality gene expression cassette, a DNA binding gene expression cassette, a selectable marker gene expression cassette, an RNAi construct expression cassette, a site-specific genome modification enzyme gene expression cassette, an expression cassette encoding a recombinant guide RNA of an RNA-guided endonuclease, or an expression cassette encoding a recombinant DNA guide. In some embodiments, the DNA of interest is integrated into the target site of the maize B chromosome via a homology directed repair integration method. In some embodiments, the DNA of interest is integrated into the target site of the maize B chromosome via a non-homologous end joining integration method. In some embodiments, the DNA of interest and/or the maize B chromosome target site sequences are modified during integration of the DNA of interest into the target site of the maize B chromosome sequence. In some embodiments, the recombinant nucleic acid is present in a maize plant, a maize plant part, a maize seed, or a maize plant cell.

Several embodiments relate to a recombinant nucleic acid comprising a nucleic acid sequence of at least 1 Kb having at least 90% sequence identity with a maize B chromosome sequence selected from the group consisting of SEQ ID NOs: 10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888, and a DNA of interest integrated into the maize B chromosome sequence to produce the recombinant nucleic acid. In some embodiments, the recombinant nucleic acid comprises one or more of the DNA of interest inserted proximal to two or more target sites for a site-specific genome modification enzyme. In some embodiments, the site-specific genome modification enzyme is an endonuclease. In some embodiments, the site-specific genome modification enzyme is a recombinase. In some embodiments, the site-specific genome modification enzyme is a transposase. In some embodiments, the site-specific genome modification enzyme is a helicase. In some embodiments, the site-specific genome modification enzyme is any combination of an endonuclease, a recombinase, a transposase and a helicase. In some embodiments, the target site is specific for maize B chromosome sequence. In a further embodiment, the target site is specific for maize B chromosome sequence is selected from one or more of the group comprising SEQ ID NOs: 10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888. In some embodiments, the site-specific genome modification enzyme is an endonuclease selected from a meganuclease, a zinc finger nuclease, a transcription activator-like effector nuclease (TALEN), an Argonaute, a DNA-guided recombinase, a DNA-guided endonuclease, an RNA-guided recombinase, an RNA-guided endonuclease, a type I CRISPR-Cas system, type II CRISPR-Cas system and a type III CRISPR-Cas system. In some embodiments, the endonuclease is selected from the group comprising Cpf1, Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4 nuclease. In some embodiments, the site-specific genome modification enzyme is an RNA-guided recombinase. In some embodiments, the site-specific genome modification enzyme is a fusion protein comprising a recombinase and a CRISPR associated protein. In some embodiments, the recombinase is a tyrosine recombinase attached to a DNA recognition motif, or a serine recombinase attached to a DNA recognition motif. In some embodiments, the recombinase is a Cre recombinase, a Flp recombinase, and a Tnp1 recombinase, a PhiC31 integrase, an R4 integrase, or a TP-901 integrase. In some embodiments, transposase is a DNA transposase attached to a DNA binding domain. In some embodiments, two or more of the DNA of interest are the same. In some embodiments, two or more of the DNA of interest are not the same. In some embodiments, the DNA of interest does not encode a peptide. In some embodiments, the DNA of interest does encode a peptide. In some embodiments, the DNA of interest comprises one or more gene expression cassettes. In some embodiments, the gene expression cassette is selected from the group comprising an insecticidal resistance gene expression cassette, an herbicide tolerance gene expression cassette, a nitrogen use efficiency gene expression cassette, a water use efficiency gene expression cassette, a nutritional quality gene expression cassette, a DNA binding gene expression cassette, a selectable marker gene expression cassette, an RNAi construct expression cassette, a site-specific genome modification enzyme gene expression cassette, an expression cassette encoding a recombinant guide RNA of an RNA-guided endonuclease, or an expression cassette encoding a recombinant DNA guide. In some embodiments, the DNA of interest is integrated into the target site of the maize B chromosome via a homology directed repair integration method. In some embodiments, the DNA of interest is integrated into the target site of the maize B chromosome via a non-homologous end joining integration method. In some embodiments, two or more of the maize B chromosome target site sequences each comprise an integrated DNA of interest to produce two or more recombinant sequences. In some embodiments, the two or more recombinant sequences are located on the same B chromosome. In some embodiments, the two or more recombinant sequences are located on different B chromosomes. In some embodiments, the two or more recombinant sequences are located on different B chromosomes which, during cell division, recombine to generate a new megalocus on a new B chromosome. In some embodiments, the DNA of interest and/or the maize B chromosome target site sequences are modified during integration of the DNA of interest into the target site of the maize B chromosome sequence. In some embodiments, the recombinant nucleic acid is present in a maize plant, a maize plant part, a maize seed, or a maize plant cell.

Several embodiments relate to a recombinant nucleic acid comprising a nucleic acid sequence of at least 1 Kb having at least 90% sequence identity with a maize B chromosome sequence selected from the group consisting of SEQ ID NOs: 10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888, and a DNA of interest integrated into the maize B chromosome sequence to produce the recombinant nucleic acid. In some embodiments, the recombinant nucleic acid comprises one or more of the DNA of interest inserted proximal to two or more target sites for a site-specific genome modification enzyme. In some embodiments, the site-specific genome modification enzyme is an endonuclease. In some embodiments, the site-specific genome modification enzyme is a recombinase. In some embodiments, the site-specific genome modification enzyme is a transposase. In some embodiments, the site-specific genome modification enzyme is a helicase. In some embodiments, the site-specific genome modification enzyme is any combination of an endonuclease, a recombinase, a transposase and a helicase. In some embodiments, the target site is specific for maize B chromosome sequence. In a further embodiment, the target site is specific for maize B chromosome sequence is selected from one or more of the group comprising SEQ ID NOs:10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888. In some embodiments, the site-specific genome modification enzyme is an endonuclease selected from a meganuclease, a zinc finger nuclease, a transcription activator-like effector nuclease (TALEN), an Argonaute, a DNA-guided recombinase, a DNA-guided endonuclease, an RNA-guided recombinase, an RNA-guided endonuclease, a type I CRISPR-Cas system, type II CRISPR-Cas system and a type III CRISPR-Cas system. In some embodiments, the endonuclease is selected from the group comprising Cpf1, Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4 nuclease. In some embodiments, the site-specific genome modification enzyme is an RNA-guided recombinase. In some embodiments, the site-specific genome modification enzyme is a fusion protein comprising a recombinase and a CRISPR associated protein. In some embodiments, the recombinase is a tyrosine recombinase attached to a DNA recognition motif, or a serine recombinase attached to a DNA recognition motif. In some embodiments, the recombinase is a Cre recombinase, a Flp recombinase, and a Tnp1 recombinase, a PhiC31 integrase, an R4 integrase, or a TP-901 integrase. In some embodiments, transposase is a DNA transposase attached to a DNA binding domain. In some embodiments, two or more of the DNA of interest are the same. In some embodiments, two or more of the DNA of interest are not the same. In some embodiments, the DNA of interest does not encode a peptide. In some embodiments, the DNA of interest does encode a peptide. In some embodiments, the DNA of interest comprises one or more gene expression cassettes. In some embodiments, the gene expression cassette is selected from the group comprising an insecticidal resistance gene expression cassette, an herbicide tolerance gene expression cassette, a nitrogen use efficiency gene expression cassette, a water use efficiency gene expression cassette, a nutritional quality gene expression cassette, a DNA binding gene expression cassette, a selectable marker gene expression cassette, an RNAi construct expression cassette, a site-specific genome modification enzyme gene expression cassette, an expression cassette encoding a recombinant guide RNA of an RNA-guided endonuclease, or an expression cassette encoding a recombinant DNA guide. In some embodiments, the DNA of interest is integrated into the target site of the maize B chromosome via a homology directed repair integration method. In some embodiments, the DNA of interest is integrated into the target site of the maize B chromosome via a non-homologous end joining integration method. In some embodiments, two or more of the maize B chromosome target site sequences each comprise an integrated DNA of interest to produce two or more recombinant sequences. In some embodiments, the two or more recombinant sequences are located on the same B chromosome. In some embodiments, the two or more recombinant sequences are located on different B chromosomes. In some embodiments, the two or more recombinant sequences are located on different B chromosomes which, during cell division, recombine to generate a new megalocus on a new B chromosome. In some embodiments, the DNA of interest and/or the maize B chromosome target site sequences are modified during integration of the DNA of interest into the target site of the maize B chromosome sequence. In some embodiments, the recombinant nucleic acid is present in a maize plant, a maize plant part, a maize seed, or a maize plant cell.

Several embodiments relate to a method of making a maize plant cell comprising a recombinant nucleic acid with a DNA of interest integrated in a B chromosome, the method comprising: (a) selecting a target site in a maize B chromosome genomic locus having at least 90% sequence identity from the group consisting of SEQ ID NOs: 10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888; (b) selecting a site specific genome modification enzyme that specifically binds and cleaves the target site in the maize B chromosome genomic locus; (c) introducing the site specific genome modification enzyme into a maize plant cell; (d) optionally, when the site-specific genome modification enzyme of step (c) is an RNA-guided endonuclease, introducing a guide RNA into a maize plant cell; or (e) optionally, when the site-specific genome modification enzyme of step (c) is an DNA-guided endonuclease, introducing a guide DNA into a maize plant cell; (e) introducing the DNA of interest into the maize plant cell; (f) integrating the DNA of interest proximal to the target site in the maize B chromosome genomic locus; and (g) selecting transgenic plant cells comprising the DNA of interest integrated into the target site of the maize B chromosome genomic locus. Several embodiments relate to a method of making a maize plant cell comprising a recombinant nucleic acid with a DNA of interest integrated in a B chromosome, the method comprising: (a) selecting a pair of target sites in a maize B chromosome genomic locus having at least 90% sequence identity from the group consisting of SEQ ID NOs: 10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888; (b) selecting one or more site specific genome modification enzymes that specifically bind and cleave the pair of target sites in the maize B chromosome genomic locus; (c) introducing the site specific genome modification enzymes into a maize plant cell; (d) optionally, when one of the site-specific genome modification enzymes of step (c) is an RNA-guided endonuclease, introducing a guide RNA into a maize plant cell; or (e) optionally, when one of the site-specific genome modification enzymes of step (c) is an DNA-guided endonuclease, introducing a guide DNA into a maize plant cell; (e) introducing the DNA of interest into the maize plant cell; (f) integrating the DNA of interest between the pair of target sites for the site-specific genome modification enzymes in a maize B chromosome genomic locus; and (g) selecting transgenic plant cells comprising at least one of the DNA of interest integrated into at least one of the target sites of the maize B chromosome genomic locus. Several embodiments relate to a method of making a maize plant cell comprising a recombinant nucleic acid with at least one DNA of interest integrated in a B chromosome, the method comprising: (a) selecting two or more target sites in a maize B chromosome genomic locus having at least 90% sequence identity from the group consisting of SEQ ID NOs: 10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888; (b) selecting one or more site specific genome modification enzymes that specifically bind and cleave the two or more target sites in the maize B chromosome genomic locus; (c) introducing the site specific genome modification enzymes into a maize plant cell; (d) optionally, when one of the site-specific genome modification enzymes of step (c) is an RNA-guided endonuclease, introducing a guide RNA into a maize plant cell; or (e) optionally, when one of the site-specific genome modification enzymes of step (c) is an DNA-guided endonuclease, introducing a guide DNA into a maize plant cell; (e) introducing the at least one DNA of interest into the maize plant cell; (f) integrating the at least one DNA of interest proximal to two or more target sites for the site-specific genome modification enzymes in a maize B chromosome genomic locus; and (g) selecting transgenic plant cells comprising at least one of the DNA of interest integrated into at least one of the target sites of the maize B chromosome genomic locus. Several embodiments relate to a method of making a maize plant cell comprising a recombinant nucleic acid with two or more DNA of interest integrated in a B chromosome, the method comprising: (a) selecting two or more target sites in a maize B chromosome genomic locus having at least 90% sequence identity from the group consisting of SEQ ID NOs: 10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888; (b) selecting one or more site specific genome modification enzymes that specifically bind and cleave the two or more target sites in the maize B chromosome genomic locus; (c) introducing the site specific genome modification enzymes into a maize plant cell; (d) optionally, when one of the site-specific genome modification enzymes of step (c) is an RNA-guided endonuclease, introducing a guide RNA into a maize plant cell; or (e) optionally, when one of the site-specific genome modification enzymes of step (c) is an DNA-guided endonuclease, introducing a guide DNA into a maize plant cell; (e) introducing the two or more DNA of interest into the maize plant cell; (f) integrating the two or more DNA of interest proximal to two or more target sites for the site-specific genome modification enzymes in a maize B chromosome genomic locus; and (g) selecting transgenic plant cells comprising at least one of the DNA of interest integrated into at least one of the target sites of the maize B chromosome genomic locus. In some embodiments, the site-specific genome modification enzyme is an endonuclease. In some embodiments, the site-specific genome modification enzyme is a recombinase. In some embodiments, the site-specific genome modification enzyme is a transposase. In some embodiments, the site-specific genome modification enzyme is a helicase. In some embodiments, the site-specific genome modification enzyme is any combination of an endonuclease, a recombinase, a transposase and a helicase. In some embodiments, the target site is specific for maize B chromosome sequence. In a further embodiment, the target site is specific for maize B chromosome sequence is selected from one or more of the group comprising SEQ ID NOs: 10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888. In some embodiments, the site-specific genome modification enzyme is an endonuclease selected from a meganuclease, a zinc finger nuclease, a transcription activator-like effector nuclease (TALEN), an Argonaute, a DNA-guided recombinase, a DNA-guided endonuclease, an RNA-guided recombinase, an RNA-guided endonuclease, a type I CRISPR-Cas system, type II CRISPR-Cas system and a type III CRISPR-Cas system. In some embodiments, the endonuclease is selected from the group comprising Cpf1, Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4 nuclease. In some embodiments, the site-specific genome modification enzyme is an RNA-guided recombinase. In some embodiments, the site-specific genome modification enzyme is a fusion protein comprising a recombinase and a CRISPR associated protein. In some embodiments, the recombinase is a tyrosine recombinase attached to a DNA recognition motif, or a serine recombinase attached to a DNA recognition motif. In some embodiments, the recombinase is a Cre recombinase, a Flp recombinase, and a Tnp1 recombinase, a PhiC31 integrase, an R4 integrase, or a TP-901 integrase. In some embodiments, transposase is a DNA transposase attached to a DNA binding domain. In some embodiments, two or more of the DNA of interest are the same. In some embodiments, two or more of the DNA of interest are not the same. In some embodiments, the DNA of interest does not encode a peptide. In some embodiments, the DNA of interest does encode a peptide. In some embodiments, the DNA of interest comprises one or more gene expression cassettes. In some embodiments, the gene expression cassette is selected from the group comprising an insecticidal resistance gene expression cassette, an herbicide tolerance gene expression cassette, a nitrogen use efficiency gene expression cassette, a water use efficiency gene expression cassette, a nutritional quality gene expression cassette, a DNA binding gene expression cassette, a selectable marker gene expression cassette, an RNAi construct expression cassette, a site-specific genome modification enzyme gene expression cassette, an expression cassette encoding a recombinant guide RNA of an RNA-guided endonuclease, or an expression cassette encoding a recombinant DNA guide. In some embodiments, the site-specific genome modification enzyme is stably transformed into the maize plant cell. In some embodiments, the site-specific genome modification enzyme is transiently transformed into the maize plant cell. In some embodiments, the site-specific genome modification enzyme is constitutively expressed in the maize plant cell. In some embodiments, the site-specific genome modification enzyme is expressed in the maize plant cell under the control of a regulatable promoter. In some embodiments, the regulatable promoter is a heat shock promoter, a tissue specific promoter, or a chemically inducible promoter. In some embodiments, the DNA of interest is integrated into the target site of the maize B chromosome via a homology directed repair integration method. In some embodiments, the DNA of interest is integrated into the target site of the maize B chromosome via a non-homologous end joining integration method. In some embodiments, two or more of the maize B chromosome target site sequences each comprise an integrated DNA of interest to produce two or more recombinant sequences. In some embodiments, the two or more recombinant sequences are located on the same B chromosome. In some embodiments, the two or more recombinant sequences are located on different B chromosomes. In some embodiments, the two or more recombinant sequences are located on different B chromosomes which, during cell division, recombine to generate a new megalocus on a new B chromosome. In some embodiments, the DNA of interest and/or the maize B chromosome target site sequences are modified during integration of the DNA of interest into the target site of the maize B chromosome sequence. In some embodiments, the recombinant nucleic acid is present in a maize plant, a maize plant part, a maize seed, or a maize plant cell.

In some embodiments, probes specific for the maize B chromosome sequence selected from the group consisting of SEQ ID NOs: 10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888 are developed. In some embodiments, the probes are generated by PCR amplification. In some embodiments, the PCR primers are selected from the group consisting of SEQ ID NO:889-894. In some embodiments, the PCR primers are used for mapping of maize B Chromosome/A Chromosome translocations. In some embodiments, the maize B chromosome sequence is used to develop maize B chromosome markers. In some embodiments, the maize B chromosome sequence is used to identify flanking sequence of transgenes integrated into a B chromosome.

Several embodiments relate to a method of identifying a sequence unique to corn B chromosome including one or more of the steps: (1) identifying a corn plant with a high copy number of B chromosome; (2) preparing DNA from tissue collected from the plant of step 1; (3) preparing a fosmid library with the DNA from step 2 and aliquot into pools; (3) sequencing the pooled fosmid library; (4) using bioinformatic analysis to extract sequence unique to corn B chromosome. In some embodiments, the corn plant with a high copy number of B chromosome is selected from a plant with 1, 2, 3, 4, 5, 6, 7, 8, 8, 10, 11, 12, 13, 14, 15, 16, 17, 18, 19, 20, or more B chromosomes. In some embodiments, bioinformatic analysis is includes: (1) extracting good quality, usable sequence of the fosmid pooled library; (2) assembling the sequence reads from step 1 into individual pool contigs; (3) analyzing and masking the individual pool contigs from step 2 for (a) known corn A chromosome non-repeat sequence from a reference corn genome assembly, (b) for known corn mitochondrial DNA sequence in a reference corn genome assembly, (c) for known corn chloroplast DNA sequence in a reference corn genome assembly; and (d) for *E. coli* and/or fosmid vector sequences; (4) analyzing the pooled sequence from step (3) against one-another to identify B chromosome repeat sequence or to filter out corn A chromosome sequence which is not in the corn reference genome assembly; and (4) comparing the resulting sequences to identify the longest representative sequence for each contig, and assembling longest contig from overlapping contigs. In further embodiments, long-read sequence is generated from the corn B chromosome DNA using single molecule, real-time sequencing technology to generate a high-quality, contiguous assembly of the genomic sequence. In further embodiments, the corn B chromosome contig assembly from the fosmid library analysis and the long-read sequence are combined to generate an assembly of unique B chromosome sequence.

DETAILED DESCRIPTION

While maize B chromosomes have been studied for many decades, a comprehensive assembly of unique maize B chromosome sequence has not been available. The present disclosure provides unique maize B chromosome sequences useful for the development of probes for B chromosome mapping, the development of B chromosome genomic markers, and identification of loci for site specific integration of a DNA of interest into B chromosomes.

Several embodiments described herein relate to methods for identifying unique maize B chromosome sequences. Such unique maize B chromosome sequences are useful for developing site-specific targeted integration of a DNA of interest at a single locus, integration two or more DNA of interest at separate loci, integration of two or more DNA of interest at a single locus, or integration of two or more DNA of interest at two or more loci. The integration of two or more DNA of interest at separate but linked loci is also known as "stacking".

Unless defined otherwise, all technical and scientific terms used have the same meaning as commonly understood by one of ordinary skill in the art to which this disclosure belongs. Where a term is provided in the singular, the inventors also contemplate aspects of the disclosure described by the plural of that term. Where there are discrepancies in terms and definitions used in references that are incorporated by reference, the terms used in this application shall have the definitions given herein. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6th edition, 2002, McGraw-Hill, New York), or the "Oxford Dictionary of Biology" (6th edition, 2008, Oxford University Press, Oxford and New York). The inventors do not intend to be limited to a mechanism or mode of action. Reference thereto is provided for illustrative purposes only.

The practice of the present disclosure employs, unless otherwise indicated, conventional techniques of biochemistry, chemistry, molecular biology, microbiology, cell biology, genomics and biotechnology, which are within the skill of the art. See Green and Sambrook, MOLECULAR CLONING: A LABORATORY MANUAL, 4th edition (2012); CURRENT PROTOCOLS IN MOLECULAR BIOLOGY (F. M. Ausubel, et al. eds., (1987)); the series METHODS IN ENZYMOLOGY (Academic Press, Inc.); PCR 2: A PRACTICAL APPROACH (M. J. MacPherson, B. D. Hames and G. R. Taylor eds. (1995)); Harlow and Lane, eds. (1988) ANTIBODIES, A LABORATORY MANUAL; ANIMAL CELL CULTURE (R. I. Freshney, ed. (1987)); RECOMBINANT PROTEIN PURIFICATION: PRINCIPLES AND METHODS, 18-1142-75, GE Healthcare Life Sciences; C. N. Stewart, A. Touraev, V. Citovsky, T. Tzfira eds. (2011) PLANT TRANSFORMATION TECHNOLOGIES (Wiley-Blackwell); and R. H. Smith (2013) PLANT TISSUE CULTURE. TECHNIQUES AND EXPERIMENTS (Academic Press, Inc.).

Any references cited herein are incorporated by reference in their entireties.

As used herein, the singular form "a," "an," and "the" include plural references unless the context clearly dictates otherwise. Thus, for example, reference to "plant," "the plant," or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

As used herein, "plant" refers to a whole plant or a cell or tissue culture derived from a plant, comprising any of: whole plants, plant components or organs (e.g., leaves, stems, roots, etc.), plant tissues, seeds, plant cells, and/or progeny of the same. A progeny plant can be from any filial generation, e.g., $F_1$, $F_2$, $F_3$, $F_4$, $F_5$, $F_6$, $F_7$, etc. A plant cell is a biological cell of a plant, taken from a plant or derived through culture from a cell taken from a plant. Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root. Plant cells, as used herein, includes protoplasts and protoplasts with a cell wall. A plant cell may be a protoplast, a gamete producing cell, or a cell or collection of cells that can regenerate into a whole plant.

As used herein, the term "about" indicates that a value includes the inherent variation of error for the method being employed to determine a value, or the variation that exists among experiments.

As used herein, "corn" and "maize" interchangeably refer to *Zea mays* L and includes all plant varieties that can be bred with corn, including wild maize species. As used herein, "corn" and "maize" can be used interchangeably.

As used herein, rye refers to *Secale cereale*.

In an aspect, a maize plant or seed provided in this disclosure is *Zea mays* L. In another aspect, a maize plant or seed provided in this disclosure is *Zea mays* ssp. mays. In yet another aspect, a maize plant or seed provided herein is a domesticated line or variety.

As used herein, the term "B chromosome" refers to an extra, or supernumerary chromosome. B chromosomes are found in addition to the normal diploid complement of chromosomes in a cell. In maize, the normal diploid complement of chromosomes is 20. The normal chromosomes can be called "A chromosomes." B chromosomes are dispensable and not required for normal development. When two B chromosomes are present in a single plant, the two B chromosomes will pair with each other at meiotic prophase and recombination can occur. B chromosomes do not pair with the A chromosomes.

In one aspect, methods of this disclosure incorporate DNAs of interest into a supernumerary chromosome. In some embodiments, methods of this disclosure incorporate DNAs of interest into a maize B chromosome sequence selected from the group consisting of SEQ ID NOs: 10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888.

One or more B chromosomes, according to certain aspects of the present disclosure, can be delivered to a progeny plant without the rest of the genome (e.g., via a haploid induction cross that retains the B chromosome), allowing complete conversion to a new variety in a single cross. In other aspects, a B chromosome may be transferred to other species, allowing testing of the DNA of interest or DNAs of interest in other crops. For example, transmission of a B chromosome to oat has been demonstrated (Koo et al., Genome Research 21(6):908-914, 2011), as well as transmission of a corn chromosome to wheat (Comeau et al., Plant Science 81(1):117-125, 1992).

In certain cases, such as in corn and rye, B chromosomes have "accumulation mechanisms" that allow them to transmit at greater than Mendelian frequencies. For example, in corn, the sister chromatids of the B chromosome fail to separate during the second pollen (first generative) division. As a result, both sister chromatids are delivered to one of the pollen cells, while the other pollen cell receives neither. This effect, called non-disjunction, means that a plant with only a single B chromosome can deliver two B chromosomes to the next generation when used as a male. Such an effect may be desirable during the trait introgression process, since it allows individuals that are homozygous (as opposed to hemizygous) for a megalocus carried on a B chromosome to be recovered in a backcross, as long as the B chromosome is delivered from the pollen.

The non-disjunction effect requires that specific portions of the B chromosome be present. A trans-acting piece at the tip of the long arm and a cis-acting piece near the centromere are required. Very small deletions at the tip of the long arm of the B chromosome are recoverable and the resulting B chromosomes do not exhibit non-disjunction. In certain embodiments of the disclosure, such a deletion variant of the B chromosome may be desired, for instance, for the purpose of delivering a megalocus for commercial traits. In other embodiments, non-disjunction may be desired, for instance, for the purpose of transiently delivering one or more site-specific genome modification enzymes that modify one or more target sequences in the A genome to produce one or more gene edits or transgene insertions and where the B chromosomes comprising the one or more site-specific genome modification enzymes are lost in subsequent generations.

Several embodiments relate to the use of B chromosomes to rapidly transfer the haploid induction effect to new lines. Because the B chromosome can be retained at a low percentage, a line where the haploid induction effect is caused by the B chromosome may allow the effect to be moved to additional lines by a single cross. This simplifies creation of new haploid induction lines with desired agronomic or genetic properties. Genetic elements disclosed in U.S. Patent Application 62/375,618 (titled Compositions and Methods for Plant Haploid Induction, filed Aug. 16, 2016) can be incorporated into a the unique B chromosome sequences described herein to produce plants containing the haploid inducing B chromosome (HI-B chromosome). The disclosure of U.S. Patent Application 62/375,618 is incorporated by reference herein in its entirety. Other haploid induction genes, e.g. the CENH3-based transgenes (Kelliher, T et al., "Maternal Haploids Are Preferentially Induced by CENH3-tailswap Transgenic Complementation in Maize", Frontiers in Plant Science 7: 414 (2016)) can also be incorporated into the unique B chromosome sequences as described herein to produce plants containing HI-B chromosome. To move the haploid induction effect to new lines, a line containing HI-B chromosome is crossed to the desired line and progeny are screened for cases that are haploid and that have retained the HI-B chromosome.

In an aspect, a B chromosome provided herein is a maize B chromosome. In an aspect, a maize B chromosome sequence or maize B chromosome genomic loci provided herein is selected from the group consisting of SEQ ID NOs: 10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888. In an aspect, a B chromosome provided herein undergoes non-disjunction. In an aspect, a B chromosome provided herein undergoes non-disjunction in a pollen cell. In another aspect, a B chromosome provided herein accumulates in a non-Mendelian manner. In an aspect, a B chromosome provided herein is truncated. In an aspect, a B chromosome provided herein can comprise one or more DNA of interest. In another aspect, a B chromosome provided herein can be used in any method provided herein. In an aspect, a B chromosome provided herein is heterogeneous. In an aspect, a B chromosome provided herein is a univalent during meiosis. In an aspect, a B chromosome provided herein pairs with a second B chromosome during meiosis. In an aspect, a B chromosome provided herein pairs with a second B chromosome during meiosis, and the first and second B chromosomes recombine creating a new B chromosome. In an aspect, a B chromosome provided herein comprises at least one, at least two, at least three, at least four, at least five, at least six, at least seven, at least eight, at least nine, or at least ten target sites for site-specific genome modification enzymes. In an aspect, a B chromosome provided herein comprises a translocation between a B chromosome and an A chromosome, where the B chromosome comprises a B chromosome centromere. In an aspect, a first B chromosome provided herein has at least 50%, at least 60%, at least 70%, at least 80%, at least 90%, at least 91%, at least 92%, at least 93%, at least 94%, at least 95%, at least 96%, at least 97%, at least 98%, at least 99%, at least 99.5%, or 100% sequence identity with a second B chromosome.

In an aspect, a plant cell provided herein can comprise one or more, two or more, three or more, four or more, five or more, six or more, seven or more, eight or more, nine or more, ten or more, fifteen or more, twenty or more, or twenty-five or more B chromosomes.

The methods described herein can be applied to extract unique B chromosome sequences of sufficient length to provide gene targeting to multiple sites, and to enable B chromosome marker development. For example, unique sequences can be used for site directed genome modification applications, including site-specific integration of a DNA of interest. The methods described herein can be applied to any genome with B chromosomes that uses a pooled bacterial artificial chromosome (BAC), a fosmid sequencing strategy, or a single molecule real time sequencing strategy.

Sequences disclosed herein can also be used to create gene editing tools to make truncated B chromosomes with altered transmission properties, which would be useful in a 1-cross trait integration strategy. Sequences disclosed herein can also be used to identify polymorphisms among different B chromosome sources, and such polymorphisms can be used to construct a genetic recombination map of the B chromosome. Sequences disclosed herein can also be used as FISH probes or in other physical mapping strategies (B-A translocation mapping) to localize sequence contigs relative to each other and other landmarks on the B chromosome (centromere, telomere, published B repeats, etc).

As used herein, "recombinant sequence" and "recombinant nucleic acid sequence" are used interchangeably.

As used herein, "inserted" and "integrated" are used interchangeably.

In some embodiments, a DNA of interest may be a transgene. In some embodiments, a DNA of interest may be a DNA molecule that is "cis-genic", which refers to a DNA sequence from the crop plant itself or from a sexually compatible donor plant. In some embodiments, a DNA of interest may comprise one or more "transgenes", where a transgene is a DNA sequence not naturally found in the maize B chromosome.

In an aspect, this disclosure provides one or more, two or more, three or more, four or more, five or more, six or more, seven or more, eight or more, nine or more, ten or more, fifteen or more, twenty or more, or twenty-five or more recombinant nucleic acid sequences comprising a nucleic acid sequence of at least 25 base pairs, at least 50 base pairs, at least 100 base pairs, at least 250 base pairs, at least 500 base pairs, at least 1000 base pairs (1 Kb), at least 1500 base pairs (1.5 Kb), at least 2000 base pairs (2 Kb), at least 2500 base pairs (2.5 Kb), at least 3000 base pairs (3 Kb), at least 3500 base pairs (3.5 Kb), at least 4000 base pairs (4 Kb), at least 4500 base pairs (4.5 Kb), at least 5000 base pairs (5 Kb), at least 5500 base pairs (5.5 Kb), at least 6000 base pairs (6 Kb), at least 6500 base pairs (6.5 Kb), at least 7000 base pairs (7 Kb), at least 7500 base pairs (7.5 Kb), at least 8000 base pairs (8 Kb), at least 8500 base pairs (8.5 Kb), at least 9000 base pairs (9 Kb), at least 9500 base pairs (9.5 Kb), or at least 10,000 base pairs (10 Kb) that has at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, or 100% sequence identity with a sequence selected from the group consisting of SEQ ID NOs: 10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888, and one or more, two or more, three or more, four or more, five or more, six or more, seven or more, eight or more, nine or more, ten or more, fifteen or more, twenty or more, or twenty-five or more DNAs of interest that can be integrated into a maize B chromosome nucleic acid sequence to produce the recombinant nucleic acid sequence. In another aspect, a recombinant nucleic acid sequence provided herein is integrated into a target site for a site-specific genome modification enzyme where the target site is specific for the maize B chromosome DNA sequence. In yet another aspect, a recombinant nucleic acid sequence provided herein is integrated between two target sites for a site-specific genome modification enzyme, where the target site is specific for the maize B chromosome DNA sequence. In another aspect, one or more, two or more, three or more, four or more, five or more, six or more, seven or more, eight or more, nine or more, ten or more, fifteen or more, or twenty or more DNAs of interest are integrated into one or more, two or more, three or more, four or more, five or more, six or more, seven or more, eight or more, nine or more, ten or more, fifteen or more, or twenty or more target sites for a site-specific genome modification enzyme, where the target site is specific for the maize B chromosome DNA sequence. In an aspect, a recombinant nucleic acid provided herein comprises a DNA of interest that encodes a peptide. In another aspect, recombinant nucleic acid provided herein comprises a DNA of interest that does not encode a peptide. In some embodiments, a recombinant nucleic acid provided herein comprises a DNA of interest that encodes one or more site specific DNA modification enzyme. In some embodiments, a recombinant nucleic acid provided herein comprises a DNA of interest that encodes one or more guide RNAs and/or a tracr RNAs. In some embodiments, a recombinant nucleic acid provided herein comprises a DNA of interest that encodes an siRNA. In some embodiments, a recombinant nucleic acid provided herein comprises a DNA of interest that encodes a microRNA.

In an aspect, this disclosure provides one or more, two or more, three or more, four or more, five or more, six or more, seven or more, eight or more, nine or more, ten or more, fifteen or more, twenty or more, or twenty-five or more recombinant nucleic acid sequences comprising one or more, two or more, three or more, four or more, five or more, six or more, seven or more, eight or more, nine or more, ten or more, fifteen or more, twenty or more, or twenty-five or more DNAs of interest integrated into one B chromosome. In another aspect, this disclosure provides one or more, two or more, three or more, four or more, five or more, six or more, seven or more, eight or more, nine or more, ten or more, fifteen or more, twenty or more, or twenty-five or more recombinant nucleic acid sequences comprising one or more, two or more, three or more, four or more, five or more, six or more, seven or more, eight or more, nine or more, ten or more, fifteen or more, twenty or more, or twenty-five or more DNAs of interest integrated into two or more, three or more, four or more, five or more, six or more, seven or more, eight or more, nine or more, or ten or more B chromosomes.

In an aspect, a DNA of interest provided herein is modified during integration into a B chromosome sequence. In another aspect, a DNA of interest provided herein is not modified during integration into a B chromosome. In an aspect, a B chromosome sequence provided herein is modified when a DNA of interest provided herein integrates into it. In another aspect, a B chromosome sequence provided herein is not modified when a DNA of interest provided herein integrates into it. In some embodiments, the DNA of interest comprises a nucleic acid sequence of at least 5 base pairs, at least 10 base pairs, at least 15 base pairs, at least 20 base pairs, at least 25 base pairs, at least 50 base pairs, at least 100 base pairs, at least 125 base pairs, at least 150 base pairs, at least 200 base pairs, at least 250 base pairs, at least 500 base pairs, at least 1000 base pairs (1 Kb), at least 1500 base pairs (1.5 Kb), at least 2000 base pairs (2 Kb), at least 2500 base pairs (2.5 Kb), at least 3000 base pairs (3 Kb), at least 3500 base pairs (3.5 Kb), that has at least 90%, at least 91%, at least 92%, at least 93%, at least 94%, at least 95%, at least 96%, at least 97%, at least 98%, at least 99%, at least 99.5%, or 100% sequence identity with a portion of sequence selected from the group consisting of SEQ ID NOs: 10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888 to promote homologous recombination between the B chromosome and the DNA of interest.

In some embodiments, the DNA of interest may comprise a modified nucleic acid sequence. As used herein, a "modified" nucleic acid sequence comprises one or more nucleotide insertions, substitutions, deletions, duplications, or inversions.

As used herein a "nucleic acid of interest", "DNA of interest", or "donor" is defined as a nucleic acid/DNA sequence that has been selected for site directed, targeted insertion into the maize genome. A nucleic acid of interest can be of any length, for example between 2 and 50,000 nucleotides in length (or any integer value therebetween or thereabove), or between about 1,000 and 5,000 nucleotides in length (or any integer value therebetween). A DNA of interest may comprise one or more gene expression cassettes that encode actively transcribed and/or translated gene sequences. In some embodiments, the DNA of interest may comprise a polynucleotide sequence which does not comprise a functional gene expression cassette or an entire gene (e.g., may simply comprise regulatory sequences such as a promoter), or may not contain any identifiable gene expression elements or any actively transcribed gene sequence. The DNA of interest may optionally contain an analytical domain. Upon integration of the DNA of interest into the maize genome, the integrated sequences are referred to as the "integrated DNA of interest" or "inserted DNA of interest". Further, the DNA of interest can be can be linear or circular, and can be single-stranded or double-stranded. It can be delivered to the cell as naked nucleic acid, as a complex with one or more delivery agents (e.g., liposomes, poloxamers, T-strand encapsulated with proteins, etc.) or contained in a bacterial or viral delivery vehicle, such as, for example, *Agrobacterium tumefaciens* or a geminivirus, respectively.

In an aspect, a DNA of interest provided herein can comprise at least one, at least two, at least three, at least four, at least five, at least six, at least seven, at least eight, at least nine, or at least ten genes. In an aspect, a DNA of interest provided herein comprises no genes. Without being limiting, a gene provided herein can include an insecticidal resistance gene, an herbicide tolerance gene, a nitrogen use efficiency gene, a water use efficiency gene, a nutritional quality gene, a DNA binding gene, a selectable marker gene, an RNAi construct, a site-specific genome modification enzyme gene, a recombinant guide RNA of a CRISPR/Cas9 system, a geminivirus based expression cassette, or a plant viral expression vector system. In an aspect, a gene provided herein comprises a promoter nucleic acid sequence. In another aspect, a structural gene provided herein does not comprise a promoter nucleic acid sequence.

Examples of suitable genes of agronomic interest envisioned by the present disclosure would include but are not limited to genes for disease, insect, or pest tolerance; herbicide tolerance; genes for quality improvements such as yield, nutritional enhancements, environmental or stress tolerances; or any desirable changes in plant physiology, growth, development, morphology or plant product(s) including starch production (U.S. Pat. Nos. 6,538,181; 6,538,179; 6,538,178; 5,750,876; 6,476,295); modified oils production (U.S. Pat. Nos. 6,444,876; 6,426,447; 6,380,462); high oil production (U.S. Pat. Nos. 6,495,739; 5,608,149; 6,483,008; 6,476,295); modified fatty acid content (U.S. Pat. Nos. 6,828,475; 6,822,141; 6,770,465; 6,706,950; 6,660,849; 6,596,538; 6,589,767; 6,537,750; 6,489,461; 6,459,018); high protein production (U.S. Pat. No. 6,380,466); fruit ripening (U.S. Pat. No. 5,512,466); enhanced animal and human nutrition (U.S. Pat. Nos. 6,723,837; 6,653,530; 6,541,259; 5,985,605; 6,171,640); or biopolymers (U.S. Pat. Nos. RE37,543; 6,228,623; 5,958,745 and U.S. Patent Publication No. US20030028917). Also environmental stress resistance (U.S. Pat. No. 6,072,103); pharmaceutical peptides and secretable peptides (U.S. Pat. Nos. 6,812,379; 6,774,283; 6,140,075; 6,080,560); improved processing traits (U.S. Pat. No. 6,476,295); improved digestibility (U.S. Pat. No. 6,531,648); low raffinose (U.S. Pat. No. 6,166,292); industrial enzyme production (U.S. Pat. No. 5,543,576); improved flavor (U.S. Pat. No. 6,011,199); nitrogen fixation (U.S. Pat. No. 5,229,114); hybrid seed production (U.S. Pat. No. 5,689,041); fiber production (U.S. Pat. Nos. 6,576,818; 6,271,443; 5,981,834; 5,869,720); and biofuel production (U.S. Pat. No. 5,998,700). Any of these or other genetic elements, methods, and transgenes can be used with the disclosure as will be appreciated by those of skill in the art in view of the instant disclosure.

A DNA of interest provided herein can also include sequences that encode for other sequences such as a messenger RNA (mRNA). An mRNA produced from a nucleic acid molecule of the present disclosure can contain a 5' untranslated (5'-UTR) leader sequence. This sequence can be derived from the promoter selected to express the gene and can be specifically modified so as to increase or decrease translation of the mRNA. A 5'-UTR can also be obtained from viral RNAs, from suitable eukaryotic genes, or from a synthetic gene sequence. Such "enhancer" sequences can be desirable to increase or alter the translational efficiency of the resultant mRNA. The present disclosure is not limited to constructs where the non-translated region is derived from both the 5'-UTR that accompanies the promoter sequence. Rather, the 5'-UTR sequence can be derived from unrelated promoters or genes (see, for example U.S. Pat. No. 5,362,865). Examples of non-translation leader sequences include maize and petunia heat shock protein leaders (U.S. Pat. No. 5,362,865), plant virus coat protein leaders, plant rubisco leaders, GmHsp (U.S. Pat. No. 5,659,122), PhDnaK (U.S. Pat. No. 5,362,865), AtAnt1, TEV (Carrington and Freed, *Journal of Virology*, (1990) 64: 1590-1597), and AGRtu.nos (GenBank Accession V00087; Bevan et al., *Nucleic Acids Research* (1983) 11:369-385). Other genetic components that serve to enhance expression or affect transcription or translational of a gene are also envisioned as genetic components.

A DNA of interest provided herein can further comprise a 3' untranslated region (3'-UTR) of a gene. The provided 3'-UTRs can contain a transcriptional terminator, or an element having equivalent function, and a polyadenylation signal that functions in plants to cause the addition of polyadenylated nucleotides to the 3' end of an RNA molecule. The DNA sequences are referred to herein as transcription-termination regions. The regions are required for efficient polyadenylation of mRNA. An RNA polymerase transcribes a coding DNA sequence through a site where polyadenylation occurs. Examples of suitable 3' regions are (1) the 3' transcribed, non-translated regions containing the polyadenylation signal of *Agrobacterium* Ti plasmid genes, such as the nopaline synthase (NOS; Fraley et al., *Proceedings of the National Academy of Sciences, USA* (1983) 80: 4803-4807) gene, and (2) plant genes such as the soybean storage protein genes and the small subunit of the ribulose-1,5-bisphosphate carboxylase (ssRUBISCO) gene. An example of a preferred 3' region is that from the ssRUBISCO E9 gene from pea (European Patent Application 0385 962).

In a DNA of interest provided herein can encode one or more site-specific genome modification enzymes. In some embodiments, one or more site-specific genome modification enzymes are selected from an endonuclease, a recombinase, a transposase, a helicase or any combination thereof. In a DNA of interest provided herein can encode one or more of a meganuclease, a zinc finger nuclease, a transcription activator-like effector nuclease (TALEN), an Argonaute, a DNA-guided recombinase, a DNA-guided endonuclease, an RNA-guided recombinase, an RNA-guided endonuclease, a type I CRISPR-Cas system, type II CRISPR-Cas system and a type III CRISPR-Cas system. In a DNA of interest provided herein can encode one or more of Cpf1, Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4 nuclease. In a DNA of interest provided herein can encode a dCas9-recombinase fusion protein. In a DNA of interest provided herein can encode one or more of a tyrosine recombinase, a serine recombinase, a Cre recombinase, a Flp recombinase, a Tnp1 recombinase, a PhiC31 integrase, an R4 integrase, or a TP-901 integrase. In a DNA of interest provided herein can encode one or more of a tracr RNA and/or a guide RNA.

In one aspect, a DNA of interest provided herein can encode a selectable, screenable, or scoreable marker gene. These genetic components are also referred to herein as functional genetic components, as they produce a product that serves a function in the identification of a transformed plant, or a product of agronomic utility. The DNA that serves as a selection or screening device can function in a regenerable plant tissue to produce a compound that would confer upon the plant tissue resistance to an otherwise toxic compound. A number of screenable or selectable marker genes are known in the art and can be used in the present disclosure. Genes of interest for use as a selectable, screenable, or scoreable marker would include, but are not limited, to β-glucuronidase (GUS), green fluorescent protein (GFP), luciferase (LUC), genes conferring tolerance to antibiotics like kanamycin (Dekeyser et al., *Plant Physiology* (1989) 90: 217-223) or spectinomycin (e.g. spectinomycin aminoglycoside adenyltransferase (aadA); U.S. Pat. No. 5,217,902), genes that encode enzymes that give tolerance to herbicides like glyphosate (e.g. 5-enolpyruvylshikimate-3-phosphate synthase (EPSPS): Della-Cioppa et al., *Bio/Technology* (1987) 5: 579-584); U.S. Pat. Nos. 5,627,061; 5,633,435; 6,040,497; 5,094,945; WO04074443, and WO04009761; glyphosate oxidoreductase (GOX; U.S. Pat. No. 5,463,175); glyphosate decarboxylase (WO05003362 and US Patent Application 20040177399; or glyphosate N-acetyltransferase (GAT): Castle et al., Science (2004) 304: 1151-1154) U.S. Patent Publication 20030083480), dalapon (e.g. dehI encoding 2,2-dichloropropionic acid dehalogenase conferring tolerance to 2,2-dichloropropionic acid (Dalapon; WO9927116)), bromoxynil (haloarylnitrilase (Bxn) for conferring tolerance to bromoxynil (WO8704181A1; U.S. Pat. No. 4,810,648; WO8900193A), sulfonyl herbicides (e.g. acetohydroxyacid synthase or acetolactate synthase conferring tolerance to acetolactate synthase inhibitors such as sulfonylurea, imidazolinone, triazolopyrimidine, pyrimidyloxybenzoates and phthalide; (U.S. Pat. Nos. 6,225,105; 5,767,366; 4,761,373; 5,633,437; 6,613,963; 5,013,659; 5,141,870; 5,378,824; 5,605,011); encoding ALS, GST-II), bialaphos or phosphinothricin or derivatives (e.g. phosphinothricin acetyltransferase (bar) conferring tolerance to phosphinothricin or glufosinate (U.S. Pat. Nos. 5,646,024, 5,561,236, 5,276,268; 5,637,489; 5,273,894; and EP 275,957), atrazine (encoding GST-III), dicamba (dicamba monooxygenase; U.S. Patent Application Publications 20030115626, 20030135879), or sethoxydim (modified acetyl-coenzyme A carboxylase for conferring tolerance to cyclohexanedione (sethoxydim) and aryloxyphenoxypropionate (haloxyfop) (U.S. Pat. No. 6,414,222), among others. Other selection procedures can also be implemented including positive selection mechanisms (e.g. use of the manA gene of *Escherichia coli*, allowing growth in the presence of mannose), and dual selection (e.g. simultaneously using spectinomycin and glufosinate, or spectinomycin and dicamba) and would still fall within the scope of the present disclosure.

In one aspect, a selectable marker provided herein is a positive selection marker. A positive selection marker confers an advantage to a transformed cell. In an aspect, a DNA of interest provided herein comprises a selectable marker gene that confers antibiotic resistance or herbicide resistance. In another aspect, a selectable marker provided herein is a negative selection marker. In another aspect, a selectable marker provided herein is both a positive selection marker and a negative selection marker. A negative selectable marker provided herein can be a lethal or non-lethal negative selectable marker. A non-lethal negative selectable marker gene can be one of any listed in U.S. Publication No. 2004-0237142, such as GGPP synthases, GA 2-oxidase gene sequences, isopentenyltransferase (IPT), CKI1 (cytokinin-independent 1), ESR-2, ESR1-A, auxin-producing genes, such as indole-3-acetic acid (IAA), iaaM, iaah, roLABC, genes that result in overexpression of ethylene biosynthetic enzymes, VP1 genes, AB13 genes, LEC1 genes, and Bas1 genes for example. A non-lethal negative selectable marker gene can be included on any nucleic acid molecule provided herein. A non-lethal negative selectable marker gene provided herein is a gene resulting in the overexpression of a class of enzymes that use substrates of the gibberellic acid (GA) biosynthetic pathway, but that do not result in the production of bioactive GA. In another aspect, a nucleic acid molecule provided herein comprises a non-lethal negative selectable marker gene such as a phytoene synthase gene from *Erwinia herbicola* (crtB).

In an aspect, a DNA of interest provided herein comprises a promoter. A promoter contains a sequence of nucleotide bases that signals RNA polymerase to associate with the DNA and to initiate transcription into mRNA using one of the DNA strands as a template to make a corresponding complementary strand of RNA. In an aspect, a promoter provided herein is a constitutive promoter. In another aspect, a promoter provided herein is a regulatable promoter. In yet another aspect, a regulatable promoter provided herein is a heat shock promoter, a tissue specific promoter, or a chemically inducible promoter.

A number of promoters that are active in plant cells have been described in the literature. Such promoters would include but are not limited to the nopaline synthase (NOS) and octopine synthase (OCS) promoters that are carried on Ti plasmids of *Agrobacterium tumefaciens*, the caulimovirus promoters such as the cauliflower mosaic virus (CaMV) 19S and 35S promoters and the Figwort mosaic virus (FMV) 35S promoter, and the enhanced CaMV35S promoter (e35S). A variety of other plant gene promoters that are regulated in response to environmental, hormonal, chemical, and/or developmental signals, also can be used for expression of heterologous genes in plant cells, including, for instance, promoters regulated by (1) heat (Callis et al., *Plant Physiology*, (1988) 88: 965-968), (2) light (e.g., pea RbcS-3A promoter, Kuhlemeier et al., *Plant Cell*, (1989) 1: 471-478; maize RbcS promoter, Schaffner et al., *Plant Cell* (1991) 3: 997-1012); (3) hormones, such as abscisic acid (Marcotte et al., *Plant Cell*, (1989) 1: 969-976), (4) wounding (e.g., Siebertz et al., *Plant Cell*, (1989) 961-968); or other signals or chemicals. Tissue specific promoters are also known.

In an aspect, a DNA of interest provided herein comprises at least one, at least two, at least three, at least four, at least five, or at least six, at least seven, at least eight, at least nine, or at least ten promoters. In an aspect, a DNA of interest provided herein does not comprise a promoter. In an aspect, a promoter provided herein can be part of a gene.

As described below, it is preferred that the particular promoter selected should be capable of causing sufficient expression to result in the production of an effective amount of the gene product of interest. Examples describing such promoters include without limitation U.S. Pat. No. 6,437, 217 (maize RS81 promoter), U.S. Pat. No. 5,641,876 (rice actin promoter), U.S. Pat. No. 6,426,446 (maize RS324 promoter), U.S. Pat. No. 6,429,362 (maize PR-1 promoter), U.S. Pat. No. 6,232,526 (maize A3 promoter), U.S. Pat. No. 6,177,611 (constitutive maize promoters), U.S. Pat. Nos. 5,322,938, 5,352,605, 5,359,142 and 5,530,196 (35S promoter), U.S. Pat. No. 6,433,252 (maize L3 oleosin promoter), U.S. Pat. No. 6,429,357 (rice actin 2 promoter as well as a rice actin 2 intron), U.S. Pat. No. 5,837,848 (root specific promoter), U.S. Pat. No. 6,294,714 (light inducible promoters), U.S. Pat. No. 6,140,078 (salt inducible promoters), U.S. Pat. No. 6,252,138 (pathogen inducible promoters), U.S. Pat. No. 6,175,060 (phosphorus deficiency inducible promoters), U.S. Pat. No. 6,635,806 (gamma-coixin promoter), and U.S. patent application Ser. No. 09/757,089 (maize chloroplast aldolase promoter). Additional promoters that can find use are a nopaline synthase (NOS) promoter (Ebert et al., 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Molecular Biology* (1987) 9: 315-324), the CaMV 35S promoter (Odell et al., *Nature* (1985) 313: 810-812), the figwort mosaic virus 35S-promoter (U.S. Pat. Nos. 6,051, 753; 5,378,619), the sucrose synthase promoter (Yang and Russell, *Proceedings of the National Academy of Sciences, USA* (1990) 87: 4144-4148), the R gene complex promoter (Chandler et al., *Plant Cell* (1989) 1: 1175-1183), and the chlorophyll a/b binding protein gene promoter, PC1SV (U.S. Pat. No. 5,850,019), and AGRtu.nos (GenBank Accession V00087; Depicker et al., *Journal of Molecular and Applied Genetics* (1982) 1: 561-573; Bevan et al., 1983) promoters.

Promoter hybrids can be constructed to enhance transcriptional activity (U.S. Pat. No. 5,106,739), or to combine desired transcriptional activity, inducibility and tissue specificity or developmental specificity. Promoters that function in plants include but are not limited to promoters that are inducible, viral, synthetic, constitutive, temporally regulated, spatially regulated, and spatio-temporally regulated. Other promoters that are tissue-enhanced, tissue-specific, or developmentally regulated are also known in the art and envisioned to have utility in the practice of this disclosure.

Promoters used in the provided nucleic acid molecules and transformation vectors of the present disclosure can be modified, if desired, to affect their control characteristics. Promoters can be derived by means of ligation with operator regions, random or controlled mutagenesis, etc. Furthermore, the promoters can be altered to contain multiple "enhancer sequences" to assist in elevating gene expression.

The present nucleic acid molecules can be incorporated into any suitable plant transformation plasmid or vector containing a selectable or screenable marker and associated regulatory elements as described, along with one or more nucleic acids encoded by a structural gene.

Site-Specific Genome Modification Enzymes

As used herein, the term "double-strand break inducing agent" refers to any agent that can induce a double-strand break (DSB) on a DNA molecule. In some embodiments, the double-strand break inducing agent is a site-specific genome modification enzyme.

As used herein, the term "site-specific genome modification enzyme" refers to any enzyme that can modify a nucleotide sequence in a site-specific manner. In the present disclosure, site-specific genome modification enzymes include endonucleases, recombinases, transposases, helicases and any combination thereof.

Several embodiments relate to promoting recombination by providing a site-specific genome modification enzyme. As used herein, the term "site-specific enzyme" refers to any enzyme that can modify a nucleotide sequence in a sequence-specific manner. In some embodiments, recombination is promoted by providing a single-strand break inducing agent. In some embodiments, recombination is promoted by providing a double-strand break inducing agent. In some embodiments, recombination is promoted by providing a strand separation inducing reagent. In one aspect, the site-specific genome modification enzyme is selected from an endonuclease, a recombinase, a transposase, a helicase or any combination thereof. In some embodiments, recombination occurs between B chromosomes. In some embodiments, recombination occurs between a B chromosome and an A chromosome. In some embodiments, recombination occurs between a DNA of interest and a unique B chromosome sequence as described herein.

Several embodiments relate to promoting integration of one or more DNAs of interest by providing a site-specific genome modification enzyme. As used herein, the term "site-specific enzyme" refers to any enzyme that can modify a nucleotide sequence in a sequence-specific manner. In some embodiments, integration of one or more DNAs of interest is promoted by providing a single-strand break inducing agent. In some embodiments, integration of one or more DNAs of interest is promoted by providing a double-strand break inducing agent. In some embodiments, integration of one or more DNAs of interest is promoted by providing a strand separation inducing reagent. In one aspect, the site-specific genome modification enzyme is selected from an endonuclease, a recombinase, a transposase, a helicase or any combination thereof.

In one aspect, the endonuclease is selected from a meganuclease, a zinc-finger nuclease (ZFN), a transcription activator-like effector nucleases (TALEN), an Argonaute (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo), an RNA-guided nuclease, such as a CRISPR associated nuclease (non-limiting examples of CRISPR associated nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof).

In some embodiments, the site-specific genome modification enzyme is a dCas9-Fok1 fusion protein. In another aspect, the site-specific genome modification enzyme is a dCas9-recombinase fusion protein. As used herein, a "dCas9" refers to a Cas9 endonuclease protein with one or more amino acid mutations that result in a Cas9 protein without endonuclease activity, but retaining RNA-guided site-specific DNA binding. As used herein, a "dCas9-recombinase fusion protein" is a dCas9 with a protein fused to the dCas9 in such a manner that the recombinase is catalytically active on the DNA.

In some embodiments, the site-specific genome modification enzyme is a recombinase. Non-limiting examples of recombinase include a tyrosine recombinase attached to a DNA recognition motif provided herein is selected from the group consisting of a Cre recombinase, a Gin recombinase a Flp recombinase, and a Tnp1 recombinase. In an aspect, a Cre recombinase or a Gin recombinase provided herein is tethered to a zinc-finger DNA-binding domain, or a TALE DNA-binding domain, or a Cas9 nuclease. In another aspect, a serine recombinase attached to a DNA recognition motif provided herein is selected from the group consisting of a PhiC31 integrase, an R4 integrase, and a TP-901 integrase. In another aspect, a DNA transposase attached to a DNA binding domain provided herein is selected from the group consisting of a TALE-piggyBac and TALE-Mutator.

Site-specific genome modification enzymes, such as meganucleases, ZFNs, TALENs, Argonaute proteins (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo), homologs thereof, or modified versions thereof), RNA-guided nucleases (non-limiting examples of RNA-guided nucleases include the CRISPR associated nucleases, such as Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof) and engineered RNA-guided nucleases (RGNs), induce a genome modification such as a double-stranded DNA break (DSB) or single-strand DNA break at the target site of a genomic sequence that is then repaired by the natural processes of homologous recombination (HR) or non-homologous end-joining (NHEJ). Sequence modifications then occur at the cleaved sites, which can include deletions or insertions that result in gene disruption in the case of NHEJ, or integration of exogenous sequences by homologous recombination.

In one aspect of the present disclosure, site-specific genome modification enzymes are selected to induce a genome modification in one, a few, or many individual target sequences of the maize B chromosome sequences provided herein. After exposure to the site-specific genome modification enzyme, the resulting recombinant nucleic acid can be identified in various ways including sequencing, PCR amplification, Southern analysis, or other molecular methods used to detect recombinant nucleic acid sequence. Site-specific genome modification enzymes may be expressed in plants such that one or more genome modifications occur within a genomic locus, and resulting progeny screened for molecular changes.

Any of the DNA of interest provided herein can be integrated into a target site of a B chromosome sequence by introducing the DNA of interest and the provided site-specific genome modification enzymes. Any method provided herein can utilize any site-specific genome modification enzyme provided herein.

ZFNs

Zinc finger nucleases (ZFNs) are synthetic proteins characterized by an engineered zinc finger DNA-binding domain fused to the cleavage domain of the FokI restriction endonuclease. ZFNs can be designed to cleave almost any long stretch of double-stranded DNA for modification of the zinc finger DNA-binding domain. ZFNs form dimers from monomers composed of a non-specific DNA cleavage domain of FokI endonuclease fused to a zinc finger array engineered to bind a target DNA sequence.

The DNA-binding domain of a ZFN is typically composed of 3-4 zinc-finger arrays. The amino acids at positions −1, +2, +3, and +6 relative to the start of the zinc finger Gα-helix, which contribute to site-specific binding to the target DNA, can be changed and customized to fit specific target sequences. The other amino acids form the consensus backbone to generate ZFNs with different sequence specificities. Rules for selecting target sequences for ZFNs are known in the art.

The FokI nuclease domain requires dimerization to cleave DNA and therefore two ZFNs with their C-terminal regions are needed to bind opposite DNA strands of the cleavage site (separated by 5-7 bp). The ZFN monomer can cute the target site if the two-ZF-binding sites are palindromic. The term ZFN, as used herein, is broad and includes a monomeric ZFN that can cleave double stranded DNA without assistance from another ZFN. The term ZFN is also used to refer to one or both members of a pair of ZFNs that are engineered to work together to cleave DNA at the same site.

Because the DNA-binding specificities of zinc finger domains can in principle be re-engineered using one of various methods, customized ZFNs can theoretically be constructed to target nearly any gene sequence. Publicly available methods for engineering zinc finger domains include Context-dependent Assembly (CoDA), Oligomerized Pool Engineering (OPEN), and Modular Assembly.

TALENs

Transcription activator-like effectors (TALEs) can be engineered to bind practically any DNA sequence. TALE proteins are DNA-binding domains derived from various plant bacterial pathogens of the genus *Xanthomonas*. The X pathogens secrete TALEs into the host plant cell during infection. The TALE moves to the nucleus, where it recognizes and binds to a specific DNA sequence in the promoter region of a specific DNA sequence in the promoter region of a specific gene in the host genome. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs. The transcription activator-like effector (TALE) DNA binding domain can be fused to a functional domain, such as a recombinase, a nuclease, a transposase or a helicase, thus conferring sequence specificity to the functional domain.

Transcription activator-like effector nucleases (TALENs) are artificial restriction enzymes generated by fusing the transcription activator-like effector (TALE) DNA binding domain to a nuclease domain. The term TALEN, as used herein, is broad and includes a monomeric TALEN that can cleave double stranded DNA without assistance from another TALEN. The term TALEN is also used to refer to one or both members of a pair of TALENs that work together to cleave DNA at the same site. In some embodiments, the nuclease is selected from a group consisting of PvuII, MutH, TevI, FokI, AlwI, MlyI, SbfI, SdaI, StsI, CleDORF, Clo051, and Pept071. When FokI is fused to a TALE domain each member of the TALEN pair binds to the DNA sites flanking a target site, the FokI monomers dimerize and cause a DSB at the target site.

Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain, and the number of bases between the two individual TALEN binding sites are parameters for achieving high levels of activity. PvuII, MutH, and TevI cleavage domains are useful alternatives to FokI and FokI variants for use with TALEs. PvuII functions as a highly specific cleavage domain when coupled to a TALE (see Yank et al. 2013. *PLoS One.* 8: e82539). MutH is capable of introducing strand-specific nicks in DNA (see Gabsalilow et al. 2013. *Nucleic Acids Research.* 41: e83). TevI introduces double-stranded breaks in DNA at targeted sites (see Beurdeley et al., 2013. *Nature Communications.* 4: 1762).

The relationship between amino acid sequence and DNA recognition of the TALE binding domain allows for designable proteins. Software programs such as DNA Works can be used to design TALE constructs. Other methods of designing TALE constructs are known to those of skill in the art. Doyle et al. (2012) TAL Effector-Nucleotide Targeter (TALE-NT) 2.0: tools for TAL effector design and target prediction. *Nucleic Acids Res.* 40(W1):W117-W122; Cermak (2011). Efficient design and assembly of custom TALEN and other TAL effector-based constructs for DNA targeting. *Nucleic Acids Res.* 39(12):e82.

Meganucleases

Meganucleases, which are commonly identified in microbes, are unique enzymes with high activity and long recognition sequences (>14 bp) resulting in site-specific digestion of target DNA. Engineered versions of naturally occurring meganucleases typically have extended DNA recognition sequences (for example, 14-40 bp).

The engineering of meganucleases is more challenging than that of ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity.

Argonaute

The Argonaute protein family is a DNA-guided endonuclease. The Argonaute isolated from *Natronobacterium gregoryi* has been reported to be suitable for DNA-guided genome editing in human cells (Gao, et al. DNA-guided genome editing using the *Natronobacterium gregoryi* Argonaute. *Nature Biotechnology* 34:768-773 (2016). Argonaute endonucleases from other species have been identified, (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo), homologs thereof, or modified versions thereof). Each of these unique Argonaute endonucleases have associated a sequence encoding DNA guide.

CRISPR

The CRISPR (clustered regularly interspaced short palindromic repeats)/Cas (CRISPR-associated) system is an alternative to synthetic proteins whose DNA-binding domains enable them to modify genomic DNA at specific sequences (e.g., ZFN and TALEN). Specificity of the CRISPR/Cas system is based on an RNA-guide that use complementary base pairing to recognize target DNA sequences. In some embodiments, the site-specific genome modification enzyme is a CRISPR/Cas system. In an aspect, a site-specific genome modification enzyme provided herein can comprise any RNA-guided Cas nuclease (non-limiting examples of RNA-guided nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof); and, optionally, the guide RNA necessary for targeting the respective nucleases.

CRISPR/Cas systems are part of the adaptive immune system of bacteria and archaea, protecting them against invading nucleic acids such as viruses by cleaving the foreign DNA in a sequence-dependent manner. The immunity is acquired by the integration of short fragments of the invading DNA known as spacers between two adjacent repeats at the proximal end of a CRISPR locus. The CRISPR arrays, including the spacers, are transcribed during subsequent encounters with invasive DNA and are processed into small interfering CRISPR RNAs (crRNAs) approximately 40 nt in length, which combine with the trans-activating CRISPR RNA (tracrRNA) to activate and guide the Cas9 nuclease. This cleaves homologous double-stranded DNA sequences known as protospacers in the invading DNA. A prerequisite for cleavage is the presence of a conserved protospacer-adjacent motif (PAM) downstream of the target DNA, which usually has the sequence 5'-NGG-3' but less frequently NAG. Specificity is provided by the so-called "seed sequence" approximately 12 bases upstream of the PAM, which must match between the RNA and target DNA. Cpf1 acts in a similar manner to Cas9, but Cpf1 does not require a tracrRNA.

As used herein, the term "target site" broadly refers to a genomic sequence selected for integration of a DNA of interest. In some aspects, the target site is in a genic region. In other aspects, the target site is in an intergenic region. In yet another aspect, the target site can include both a genic region and an intergenic region. In one aspect, a target site provided herein is recognized and cleaved by a double-strand break inducing agent, such as a site-specific genome modification enzyme, a site specific recombinase, or a site specific transposase. In some embodiments, a target site comprises a nucleic acid sequence of having at least 90%, at least 91%, at least 92%, at least 93%, at least 94%, at least 95%, at least 96%, at least 97%, at least 98%, at least 99%, or 100%, sequence identity to a portion of a maize B chromosome sequence selected from the group consisting of SEQ ID NOs:10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888.

As used herein, the term "recombination" refers to the exchange of nucleotide sequences between two DNA molecules.

As used herein, the term "homologous recombination" refers to the exchange of nucleotide sequences at a conserved region shared by two genomic loci. Homologous recombination includes symmetric homologous recombination and asymmetric homologous recombination. Asymmetric homologous recombination may also be referred to as unequal recombination.

Methods for detecting recombination include, but are not limited to, 1) phenotypic screening, 2) molecular marker technologies such as single nucleotide polymorphism (SNP) analysis by TaqMan® or Illumina/Infinium PCR technology, 3) Southern blot analysis, and 4) sequencing (e.g., Sanger, Illumina, 454, Pac-Bio, Ion Torrent). One example of a method for identifying integration of a DNA of interest in a chromosome is inverse PCR (iPCR).

In an aspect, integration of a DNA of interest provided herein occurs via homologous recombination (HR). In another aspect, integration of a DNA of interest provided herein occurs via non-homologous end joining (NHEJ).

As used herein, "transgenic" means a plant or seed whose genome has been altered by the stable integration of recombinant DNA. A transgenic line includes a plant regenerated from an originally-transformed plant cell and progeny transgenic plants from later generations or crosses of a transformed plant. As used herein, "exogenous" is intended to refer to genes that are not normally present in the cell being transformed, or not present in the form, structure, etc., as found in the transforming DNA segment or gene. Thus, the term "exogenous" gene or DNA is intended to refer to any gene or DNA segment that is introduced into a recipient cell, regardless of whether a similar gene can already be present in such a cell. The type of DNA included in the exogenous DNA can include DNA that is already present in the plant cell, DNA from another plant, DNA from a different organism, or a DNA generated externally, such as a DNA sequence containing an antisense message of a gene, or a DNA sequence encoding a synthetic or modified version of a gene.

Methods of transforming plant cells are well known by persons of ordinary skill in the art. For instance, specific instructions for transforming plant cells by microprojectile bombardment with particles coated with recombinant DNA are found in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn) and U.S. Pat. No. 6,153,812 (wheat); U.S. Pat. No. 6,002,070 (rice); U.S. Pat. No. 7,122,722 (cotton); U.S. Pat. No. 6,051,756 (*Brassica*); U.S. Pat. No. 6,297,056 (*Brassica*); US Patent Publication 20040123342 (sugarcane) and *Agrobacterium*-mediated transformation is described in U.S. Pat. No. 5,159,135 (cotton); U.S. Pat. No. 5,824,877 (soybean); U.S. Pat. No. 5,591,616 (corn); U.S. Pat. No. 6,384,301 (soybean); U.S. Pat. No. 5,750,871 (*Brassica*); U.S. Pat. No. 5,463,174 (*Brassica*) 5,188,958 (*Brassica*), all of which are incorporated herein by reference. Methods for transforming other plants can be found in, for example, Compendium of Transgenic Crop Plants (2009) Blackwell Publishing. Any appropriate method known to those skilled in the art can be used to transform a plant cell with any of the provided nucleic acid molecules. As used herein, "stably transformed" is defined as a transfer of DNA into genomic DNA of a targeted cell that allows the targeted cell to regenerate into a whole organism and pass the transferred DNA to the next generation of the transformed organism. Stable transformation requires the integration of transferred DNA within the reproductive cell(s) of the transformed organism. As used herein, "transiently transformed" is defined as a transfer of DNA into a cell that is not transferred to the next generation of the transformed organism. Transient transformations are often transformations of leaf or root (e.g., non-reproductive)

tissue in plants. The transformed DNA does not typically integrate into the transformed cell's genomic DNA during a transient transformation. In one aspect, a method provided herein stably transforms a plant cell. In another aspect, a method provided herein transiently transforms a plant cell.

In an aspect, this disclosure provides methods for transforming a plant cell with a nucleic acid sequence encoding a site-specific genome modification enzyme. In an aspect, a method provided herein comprises the stable transformation of a nucleic acid sequence encoding a site-specific genome modification enzyme. In another aspect, a method provided herein comprises the transient transformation of a nucleic acid sequence encoding a site-specific genome modification enzyme. In an aspect, a method provided herein comprises a constitutively expressed nucleic acid encoding a site-specific genome modification enzyme. In another aspect, a method provided herein comprises a nucleic acid sequence encoding a site-specific genome modification enzyme under the control of a regulatable promoter.

In an aspect of the present disclosure, a recombinant nucleic acid sequence provided herein is capable of being fully integrated into a chromosome.

In one aspect, transformation of a plant cell is performed by an *Agrobacterium*-mediated method, and the nucleic acid molecules of interest are present on one or more Integrated DNA sequences (U.S. Pat. Nos. 6,265,638, 5,731,179; U.S. Patent Application Publications US2005/0183170; 2003110532) or other nucleic acid sequence (e.g., vector backbone) that is transferred into a plant cell. The sequences that can be transferred into a plant cell can be present on one transformation vector in a bacterial strain being utilized for transformation. In another aspect, the sequences can be present on separate transformation vectors in the bacterial strain. In yet another aspect, the sequences can be found in separate bacterial cells or strains used together for transformation.

A "transformation vector," as used herein, is plasmid DNA that is capable of transforming a plant cell. In an aspect, a transformation vector provided herein can comprise any DNA of interest provided herein. In another aspect, a transformation vector provided herein can comprise any nucleic acid molecule provided herein.

The DNA constructs used for transformation in the methods of present disclosure generally also contain the plasmid backbone DNA segments that provide replication function and antibiotic selection in bacterial cells, for example, an *Escherichia coli* origin of replication such as ori322, an *Agrobacterium* origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, LBA4404, AGLO, AGL1, EHA101, or EHA105 carrying a plasmid having a transfer function for the expression unit. Other strains known to those skilled in the art of plant transformation can function in the present disclosure.

To confirm the presence of exogenous DNA or a "transgene(s)" in a transgenic cell a variety of assays can be performed. Such assays include, for example, "molecular biological" assays, such as Southern and northern blotting and PCR, "biochemical" assays, such as detecting the presence of a protein product, e.g., by immunological means (ELISAs and western blots) or by enzymatic function (e.g. GUS assay); pollen histochemistry; plant part assays, such as leaf or root assays; and also, by analyzing the phenotype of the whole regenerated plant.

This disclosure provides a method of making a transgenic plant cell comprising a DNA of interest, where the method comprises selecting a target B chromosome genomic locus having at least 70%, at least 75%, at least 80%, at least 85%, at least 90%, at least 91%, at least 92%, at least 93%, at least 94%, at least 95%, at least 96%, at least 97%, at least 98%, at least 99%, at least 99% or 100% sequence identity to any sequence selected from SEQ ID NOs:10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888, selecting a site-specific genome modification enzyme that specifically binds and cleaves the target B chromosome genomic locus; introducing the site-specific genome modification enzyme into a plant cell; introducing a DNA of interest into a plant cell; and inserting the DNA of interest into the target B chromosome genomic locus; and selecting plant cells comprising the DNA of interest integrated into the target site of the B chromosome locus. In an aspect, a method provided herein uses homology directed repair integration to integrate a DNA of interest into a B chromosome genomic locus. In another aspect, a method provided herein uses non-homologous end joining integration to integrate a DNA of interest into a B chromosome genomic locus.

In an aspect, a method provided herein integrates one or more, two or more, three or more, four or more, five or more, six or more, seven or more, eight or more, nine or more, ten or more, fifteen or more, twenty or more, or twenty-five or more DNAs of interest into one or more, two or more, three or more, four or more, five or more, six or more, seven or more, eight or more, nine or more, ten or more, fifteen or more, twenty or more, or twenty-five or more B chromosome genomic loci located on one B chromosome. In another aspect, a method provided herein integrates one or more, two or more, three or more, four or more, five or more, six or more, seven or more, eight or more, nine or more, ten or more, fifteen or more, twenty or more, or twenty-five or more DNAs of interest into one or more, two or more, three or more, four or more, five or more, six or more, seven or more, eight or more, nine or more, ten or more, fifteen or more, twenty or more, or twenty-five or more B chromosome genomic loci located on two ore more, three or more, four or more, five or more, six or more, seven or more, eight or more, nine or more, or ten or more B chromosomes.

In an aspect, a method of making a transgenic plant cell provided herein comprises a DNA of interest that is modified during integration into a B chromosome sequence. In another aspect, a method of making a transgenic plant cell provided herein comprises a B chromosome sequence that is modified when a DNA of interest provided herein integrates into it.

In an aspect, this disclosure provides a method of making a transgenic plant cell where two or more, three or more, four or more, five or more, six or more, seven or more, eight or more, nine or more, ten or more, fifteen or more, twenty or more, or twenty-five or more DNAs of interest are integrated into two or more, three or more, four or more, five or more, six or more, seven or more, eight or more, nine or more, ten or more, fifteen or more, twenty or more, or twenty-five or more target B chromosome genomic loci on separate B chromosomes; and where the B chromosomes recombine such that the two or more, three or more, four or more, five or more, six or more, seven or more, eight or more, nine or more, ten or more, fifteen or more, twenty or more, or twenty-five or more target B chromosome genomic loci generate a megalocus comprising the two or more, three or more, four or more, five or more, six or more, seven or more, eight or more, nine or more, ten or more, fifteen or more, twenty or more, or twenty-five or more DNAs of interest.

As used herein, a "megalocus" refers to a block of genetically linked transgenic traits that are normally inherited as a single unit. A megalocus according to the disclosure may provide to a plant one or more desired traits, which may include, but are not limited to, enhanced growth, drought tolerance, salt tolerance, herbicide tolerance, insect resistance, pest resistance, disease resistance, and the like. In specific embodiments, a megalocus comprises at least about 2, 3, 4, 5, 6, 7, 8, 9, 10, 11, 13 or 15 transgenic loci (events) that are physically separated but genetically linked such that they can are inherited as a single unit. Each transgenic locus in the megalocus can be 0.1, 0.2, 0.3, 0.4, 0.5, 0.6, 0.7, 0.8, 0.9, 1, 1.5, 2, 2.5, 3, 5, 10, 15, or 20 al apart from one another. In some embodiments, a megalocus comprises at least about 2, 3, 4, 5, 6, 7, 8, 9, 10, 11, 13 or 15 transgenic loci (events) that are not genetically linked but are located on the same B chromosome.

As used herein, a centimorgan ("cM") is a unit of measure of recombination frequency and genetic distance between two loci. One cM is equal to a 1% chance that a marker at one genetic locus will be separated from a marker at, a second locus due to crossing over in a single generation.

As used herein, "closely linked" means that the marker or locus is within about 20 cM, 15 cM, 10 cM, 5 cM, 4 cM, 3 cM, 2 cM, 1 cM, 0.5 cM or less than 0.5 cM of another marker or locus. For example, 20 cM means that recombination occurs between the marker and the locus with a frequency of equal to or less than about 20%.

As used herein, "proximal" refers to relative location of two nucleic acid sequences. In one aspect, a first nucleic acid sequence is proximal to a second nucleic acid sequence if the two nucleic acid sequences are separated by less than 50,000 base pairs, less than 25,000 base pairs, less than 15,000 base pairs, less than 10,000 base pairs, less than 7500 base pairs, less than 5000 base pairs, less than 4000 base pairs, less than 3000 base pairs, less than 2500 base pairs, less than 2000 base pairs, less than 1500 base pairs, less than 1000 base pairs, less than 750 base pairs, less than 500 base pairs, less than 250 base pairs, less than 100 base pairs, less than 75 base pairs, less than 50 base pairs, less than 40 base pairs, less than 30 base pairs, less than 20 base pairs, less than 10 base pairs, less than 5 base pairs, less than 3 base pairs, or 1 base pair.

In one aspect, this disclosure provides plant cells that are not reproductive material and do not mediate the natural reproduction of the plant. In another aspect, this disclosure also provides plant cells that are reproductive material and mediate the natural reproduction of the plant. In another aspect, this disclosure provides plant cells that cannot maintain themselves via photosynthesis. In another aspect, this disclosure provides somatic plant cells. Somatic cells, contrary to germline cells, do not mediate plant reproduction.

Provided plant cells or plant parts can be from seed, fruit, leaf, cotyledon, hypocotyl, meristem, embryos, endosperm, root, shoot, stem, pod, flower, inflorescence, stalk, pedicel, style, stigma, receptacle, petal, sepal, pollen, anther, filament, ovary, ovule, pericarp, phloem, bud, or vascular tissue. In another aspect, this disclosure provides a plant chloroplast. In a further aspect, this disclosure provides an epidermal cell, a stomata cell, a trichrome cell, a root hair cell, a storage root cell, or a tuber cell. In another aspect, this disclosure provides a protoplast cell. In another aspect, this disclosure provides a plant callus cell. In an aspect, any plant, plant part, or plant cell provided herein can comprise any recombinant sequence provided herein.

Nucleic acid molecules provided herein include deoxynucleic acids (DNA) and ribonucleic acids (RNA) and functional analogues thereof, such as complementary DNA (cDNA). Nucleic acid molecules provided herein can be single stranded or double stranded. Nucleic acid molecules comprise the nucleotide bases adenine (A), guanine (G), thymine (T), cytosine (C). Uracil (U) replaces thymine in RNA molecules. The symbol "N" can be used to represent any nucleotide base (e.g., A, G, C, T, or U). As used herein, "complementary" in reference to a nucleic acid molecule or nucleotide bases refers to A being complementary to T (or U), and G being complementary to C. Two complementary nucleic acid molecules are capable of hybridizing with each other. As an example, the two strands of double stranded DNA are complementary to each other. In an aspect of the present disclosure, two nucleic acid sequences are homologous, or essentially homologous, if they have at least 70%, at least 75%, at least 80%, at least 85%, at least 90%, at least 95%, at least 96%, at least 97%, at least 98%, at least 99% or 100% sequence identity with each other. A polynucleotide molecule of the present disclosure comprises at least 2, at least 5, at least 10, at least 20, at least 30, at least 40, at least 50, at least 100, at least 250, at least 500, at least 1000, at least 1500, at least 2000, at least 2500, or at least 3000 nucleotide bases. As used herein, "encoding" refers to a polynucleotide encoding for the amino acids of a polypeptide. A series of three nucleotide bases encodes one amino acid. As used herein, "expressed," "expression," or "expressing" refers to transcription of RNA from a DNA molecule. In an aspect, expression of a DNA of interest provided herein requires a promoter. In another aspect, expression of a DNA of interest provided herein does not require a promoter. In an aspect, an expressed transcript provided herein is spliced. In another aspect, an expressed transcript provided herein is not spliced.

As used herein, terms "polypeptide", "peptide" and "protein" are used interchangeably to refer to a polymer of amino acid residues. The term also applies to amino acid polymers in which one or more amino acids are chemical analogues or modified derivatives of a corresponding naturally-occurring amino acids.

In an aspect of the present disclosure, a nucleic acid sequence can be physically linked to another nucleic acid sequence, operably linked to another nucleic acid sequence or both physically and operably linked to another nucleic acid sequence. As used herein, physically linked means that the physically linked nucleic acid sequences are located on the same nucleic acid molecule. A physical linkage can be adjacent or proximal. A nucleic acid sequence provided herein can be adjacent to another nucleic acid sequence. As used herein, operably linked means that the operably linked nucleic acid sequences exhibit their desired function. For example, in an aspect of this disclosure, a provided DNA promoter sequence can initiate transcription of an operably linked DNA sequence into RNA. A nucleic acid sequence provided herein can be upstream or downstream of a physically or operably linked nucleic acid sequence. As used herein, upstream means the nucleic acid sequence is positioned before the 5' end of a linked nucleic acid sequence. As used herein, downstream means the nucleic acid sequence is positioned after the 3' end of a linked nucleic acid sequence. As used herein, 5' means the start of a coding DNA sequence or the beginning of an RNA molecule. As used herein, 3' means the end of a coding DNA sequence or the end of an RNA molecule. As used herein, "opposing side" refers to the 5' or 3' side of a nucleic acid molecule. For example, a first nucleic acid molecule sequence on the 5' side of a second nucleic acid molecule is on the opposing side of a third nucleic acid molecule sequence on the 3' end of the second nucleic acid molecule.

In an aspect, a nucleic acid molecule provided herein is a transformation vector. In an aspect, a transformation vector is a bacterial plasmid. As used herein, a "plasmid" is a DNA molecule that is physically separate from chromosomal DNA and has the ability to replicate. In another aspect, the bacterial plasmid is an *Agrobacterium* tumor-inducing (Ti) plasmid. In another aspect, a transformation vector is a synthetic plasmid. As used herein, a "synthetic plasmid" is an artificially created plasmid that is capable of the same functions (e.g. replication) as a natural plasmid (e.g. Ti plasmid). Without being limited, one skilled in the art can create a synthetic plasmid de novo via synthesizing a plasmid by individual nucleotides, or by splicing together nucleic acid molecules from different pre-existing plasmids.

EXAMPLES

Example 1: Obtaining Unique Maize B Chromosome Sequence

To identify sequences unique to the maize B chromosome, the following approach was undertaken. A line backcrossed multiple times to B73 maize containing multiple B chromosomes (referred to as B73 plus) was obtained from the University of Missouri and grown from seed in a greenhouse using standard potting and growth conditions. Due to the non-Mendelian segregation of B chromosomes, root tip tissue was collected from each individual plant grown from the B73 plus seed. The root tip tissue sample was used to create a chromosomal smear for karyotyping essentially as described by Kato et al (2011) Chromosome Painting for Plant Biotechnology, *Plant Chromosome Engineering in Methods in Molecular Biology*, ed. J. A. Birchler 701, 67-96. These chromosomal smears, stained with the chromosomal counterstain 4',6-diamidino-2-phenylindole (DAPI), were scored visually to determine the number of B chromosomes per individual nucleus. See, e.g., FIG. 1. From this data, at least one plant was identified as containing 20 individual B chromosomes per nucleus.

Leaf tissue was also collected from each plant and genomic DNA extracted. The genomic DNA was used in a Taqman® PCR copy number assay to confirm the B chromosome number in each individual plant. For this assay, a B chromosome specific marker and an A chromosome specific gene (alcohol dehydrogenase (ADH)) were amplified in the same PCR reaction. Controls included a B73 plant without B chromosomes, and 4 plants of a non-B73 germplasm with 1, 2, 3, or 4 copies of B chromosome. The ratio of signal for the B chromosome specific probe to the A chromosome specific ADH probe gave a nearly linear result when graphed. The individual plant identified by karyotyping as having 20 copies of B chromosome was consistent with the Taqman PCR copy number assay to have 20 copies of B chromosome. See Table 1.

By leveraging the 20× representation of the B chromosome to A chromosome in the DNA extracted from the identified plant with 20 copies of B chromosomes, it was recognized that a fosmid sequencing strategy could be used to identify unique B chromosome sequence by sequencing maize chromosomal DNA fragments and extracting high confidence non-repetitive unique B sequences from the data.

TABLE 1

Correlation of B chromosome copy number as determined by karyotyping to relative B marker value determined by Taqman PCR assay

| # of B chromosomes confirmed by karyotype | relative B marker value (B marker normalized to ADH control marker) |
| --- | --- |
| 0 | 0.0 |
| 0 | 0.0 |
| 0 | 0.1 |
| 0 | 0.0 |
| 0 | 0.0 |
| 0 | 0.0 |
| 0 | 0.0 |
| 0 | 0.0 |
| 0 | 0.2 |
| 0 | 0.0 |
| 0 | 0.0 |
| 0 | 2.9 |
| 1 | 25.8 |
| 1 | 47.3 |
| 1 | 36.2 |
| 1 | 34.8 |
| 1 | 42.0 |
| 2 | 87.0 |
| 3 | 112.5 |
| 4 | 128.6 |
| 4 | 138.8 |
| 4 | 150.0 |
| 6 | 175.4 |
| 6 | 97.6 |
| 6 | 231.4 |
| 6 | 84.3 |
| 7 | 311.8 |
| 7 | 252.2 |
| 7 | 66.0 |
| 7 | 242.4 |
| 7 | 224.4 |
| 8 | 262.6 |
| 8 | 326.8 |
| 8 | 347.3 |
| 8 | 328.3 |
| 9 | 326.9 |
| 9 | 306.7 |
| 9 | 305.2 |
| 10 | 390.2 |
| 11 | 406.5 |
| 13 | 482.2 |
| 14 | 496.4 |
| 14 | 576.9 |
| 16 | 661.5 |
| 20 | 744.6 |

Leaf tissue was collected from the individual plant with 20 B chromosome copies and genomic DNA was extracted using a modified CTAB method where 0.8 g of plant tissue was ground by mechanical milling, the powder was transferred to a 50 ml tube with 20 ml of extraction buffer (1.5% cetyltrimethylammonium bromide (CTAB) (Sigma-Aldrich, Saint Louis, Mo.); 75 mM Tris-HCl (pH8.0); 15 mM EDTA (pH8.0) and 1M NaCl) and the mixture was incubated in a water bath shaker at 56° C. for 20 minutes. Following incubation, the tube was centrifuged and the upper, DNA-containing, layer was transferred to a new tube. Extraction was accomplished by adding 1/10 volume of 10% CTAB (10% Cetyltrimethylammonium bromide (CTAB) and 0.7 M NaCl) and an equal volume of chloroform/iso-amyl alcohol (24:1), and this was mixed by rotating and inverting for 20 minutes, followed by centrifugation. The upper layer was transferred to a new tube and an equal volume of isopropyl alcohol was added. This was centrifuged to pellet the DNA, and the supernatant was discarded. The DNA pellet was resuspended in 5 ml 1M NaCl and 5 ul 10 mg/ml RNase, and then the DNA reprecipitated by addition of 2 volumes of ethanol. The DNA pellet was washed twice with 5 ml per wash of 70% ethanol and the final DNA pellet was resuspended in 1 mM Tris-HCl+0.1 mM EDTA (pH8.0).

The genomic DNA isolated from the plant with 20 B chromosome copies was then used to prepare a fosmid library using the CopyRight® v2.0 Fosmid Cloning Kit (Lucigen Corporation, Middleton, Wis.). The fosmid constructs contained inserts of up to about 40 kb of maize genomic sequence per construct. The fosmid constructs were pooled into 192 pools, each with approximately 1000 fosmid clones per pool. Fosmid DNA was extracted from each pool and subjected to Illumnia® sequencing following the manufacturer's protocol. Based on this sequencing, 162 of the 192 pools contained usable sequence or 'reads'. The reads from each of the 162 pools were assembled separately using assembly software tools PCAP ("Application of a superword array in genome assembly" Xiaoqiu Huang et. al Nucleic Acids Research, 2006, Vol. 34, No. 1 201-205) and CLCbio assembly cell (www.cicbio.com/products/clc-assembly-cell; Qiagen, Waltham, Mass.), and the sequence repeats for each well were masked by utilizing A chromosome repeats from a known maize genomic repeat library (maize repeats library available at Smit, A F A, Hubley, R & Green, P RepeatMasker Open-4.0. 2013-2015, www.repeatmasker.org). Next, the assembled sequence from each pool was used to filter-out A chromosome-specific non-repeat sequences by comparing the fosmid pool sequence assemblies to the maize reference B73 genome (Schnable et al., (2009) The B73 Maize Genome: Complexity, Diversity, and Dynamics. Science 326, 1112-5) (representing the maize A chromosome sequence) using alignment software Cross Match (with parameters -minmatch 17 -minscore 200 -tags -masklevel 0 -penalty -3), Phil Green, www.phrap.org/phredphrapconsed.html and using Monsanto in house scripts to parse the alignments outputs and to trim and to filter out matched chromosome A sequences. Also, the B73 mitochondrial (NCBI Reference Sequence: NC_007982.1) and chloroplast (NCBI Reference Sequence: NC_001666.2) genomic DNA was filtered out in this process. The next step was to align the sequence of each pool against the other 161 pools such that all pools were individually compared to one-another. This analysis was done to filter out "B-chromosome repeats" which were identified by a sequence that occurred in 130 or more wells, or to filter out "A-chromosome sequence which is not in the reference data set" which was identified by a sequence that occurred only one to three times across all of the pools. Finally, the remaining sequences were compared to find the longest representative sequence for each of the contig groups with multiple matches among contigs in the group. The contig sequences that were greater than 2 kb are identified as unique sequences (SEQ ID NOs: 10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, and 787-791) to the maize B-chromosome.

Example 2: Maize B Chromosome Reference Assembly

To generate a B chromosome reference assembly, the genomic DNA from the B73 plant containing 20 B chromosome copies was prepared for PacBio® sequencing following the manufacturer's protocols. The PacBio sequencing generates long-read sequence to generate high-quality, contiguous assembly of the genome. The long-read B chromosome sequence data was combined with the unique B chromosome sequence generated from the fosmid library sequencing and analysis, as described in Example 1. The combined data sets were used to generate B reference chromosome assembly sequences 792-889. This B reference chromosome can be used to map small RNA and DNA methylation patterns, to identify novel maize genes and their respective promoters, introns, terminators, and insulators, to develop new B chromosome markers, to physically map the new B chromosome markers, to enable experiments to measure recombination that might occur between B chromosomes, and to design gene editing tools such as TALENs, CRISPRs, Cpf1, Zinc fingers, or meganucleases.

Example 3: Site-Directed Genome Modification of Maize B Chromosome

The maize B chromosome sequences identified herein are used for site-directed genome modification. A meganuclease is engineered to target one of the unique maize B chromosome sites selected from a sequence in any one of SEQ ID NOs: 10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888. A maize cell is contacted with (1) the meganuclease under conditions to allow double-strand break at the selected site, and with (2) a donor DNA molecule comprising a sequence of interest to be integrated into the selected site. The donor DNA molecule may integrate by non-homologous end joining (NHEJ), or the donor DNA molecule may integrate by homologous recombination.

Alternatively, a TALEN is engineered to target one of the unique maize B chromosome sites selected from a sequence in any one of SEQ ID NOs:10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888. A maize cell is contacted with (1) the TALEN under conditions to allow double-strand break at the selected site, and with (2) a donor DNA molecule comprising a sequence of interest to be integrated into the selected site. The donor DNA molecule may integrate by non-homologous end joining (NHEJ), or the donor DNA molecule may integrate by homologous recombination. The TALEN may be a single molecule or may function as a pair of molecules.

Alternatively, an RNA guided DNA nuclease, such as CRISPR-Cas9 or Cpf1 endonuclease are used to target one of the unique maize B chromosome sites selected from a sequence in any one of SEQ ID NOs:10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888. A maize cell is contacted with (1) the CRISPR and Cas9 endonuclease, or Cpf1 endonuclease under conditions to allow double-strand break at the selected site, and with (2) a donor DNA molecule comprising a sequence of interest to be integrated into the selected site. The donor DNA molecule may integrate by non-homologous end joining (NHEJ), or the donor DNA molecule may integrate by homologous recombination.

The donor DNA may comprise one or more gene expression cassettes, wherein the gene expression cassettes have one or more expression elements (e.g., promoter, intron, targeting peptide, 3'-untranslated region/termination signal) to allow expression of a protein and/or RNA of interest in a plant cell. The protein of interest may be encoded by an insecticidal resistance gene, an herbicide tolerance gene, a nitrogen use efficiency gene, a water use efficiency gene, a nutritional quality gene, a DNA binding gene, a selectable marker gene, a transcription factor gene, a site specific endonuclease gene, a meganuclease gene, a DNA targeted recombinase gene or a gene encoding an RNA-guided endonuclease, such as, Cas9 or Cpf1. In some instances, the donor DNA may encode one or more of an RNAi construct, a guide sequence capable of hybridizing to a target sequence, a tracr mate sequence and a tracr sequence.

The maize B chromosome sequences identified herein are used for genome editing. One or more sites are selected from a sequence in any one of SEQ ID NOs:10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888. The one or more sites are targeted with an engineered site-specific meganuclease, endonuclease, or DNA targeted recombinase. Then, a maize cell is contacted with (1) the engineered site-specific meganuclease, endonuclease, or DNA targeted recombinase under conditions to allow double-strand break at the selected genomic site, and DNA is deleted or inserted (indels), or a DNA base is changed.

Example 4: Maize B Chromosome Probe Development

The maize B chromosome sequences identified herein were used to develop maize B chromosome specific PCR primer sets. For example, Table 2 details three sets of PCR primers which amplify a region of B chromosome specific sequence from SEQ ID NO:175, 177, and 183. Specifically, PCR primer pair SEQ ID NO:889 and SEQ ID NO:890 amplify a region at the coordinates 2626-2825 of SEQ ID NO:175; PCR primer pair SEQ ID NO:891 and SEQ ID NO:892 amplify a region at the coordinates 1170-1368 of SEQ ID NO:177; and PCR primer pair SEQ ID NO:893 and SEQ ID NO:894 amplify a region at the coordinates 1118-1319 of SEQ ID NO:183. A control set of PCR primers SEQ ID NO:895 and SEQ ID NO:896 for a proximal B chromosome region, labeled BCHR0004, were identified from the sequence DU978594.1 pCL7T-2 CL-repeat reported by Cheng et al. *Chromosome Research* (2010) 18:605-619. A control set of PCR primers SEQ ID NO:897 and SEQ ID NO:898 for a proximal euchromatin region 2/distal heterochromatin region 1, labeled BCHR0006, were identified from the sequence DU820494 pCL38T-2 CL-repeat DH1 reported by Cheng et al. *Chromosome Research* (2010) 18:605-619. And, a control set of PCR primers SEQ ID NO:899 and SEQ ID NO:900 for a distal heterochromatin regions 3-4 B chromosome region, labeled BCHR0007, were identified from the StarkB repeat sequence reported by Lamb et al. *Chromosome Research* (2007) 15:383-398.

TABLE 2

B chromosome specific PCR primers

| SEQ ID NO of PCR primer 1 | SEQ ID NO of PCR primer 2 | PCR primers amplify region in SEQ ID NO | Coordinates of PCR amplicon |
|---|---|---|---|
| 889 | 890 | 175 | 2624-2825 |
| 891 | 892 | 177 | 1170-1368 |
| 893 | 894 | 183 | 1118-1319 |

The PCR amplicons were mapped to the B chromosome using previously characterized B-A translocation lines. Corn with B-A translocation events were acquired from the Maize Genetics Coop Stock Center (www.maizegdb.org/stock_catalog). The samples used for testing the primers and control B-specific probes were tertiary trisomic lines containing the B-A translocation (in addition to two normal A chromosomes), but not the reciprocal A-B translocation. Because of transmission issues, the Maize Genetics Coop stock center maintains these B-A translocations as heterozygotes. Thus, the seed packet delivered does not always contain tertiary trisomic material. If that is the case, then the translocation heterozygote (verified by FISH screening from the packet received from the coop) was crossed to a tester germplasm with a tester line, and color markers were used to identify likely tertiary trisomics in the F1 generation, which were then grown and sampled.

Figure 2:
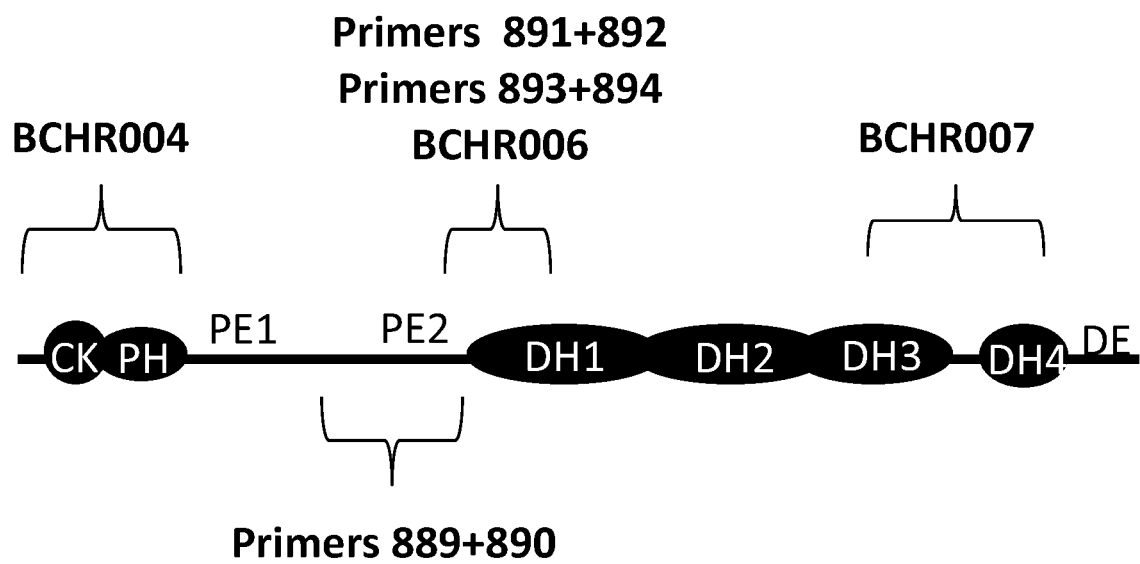
FIG. 2. Mapping of maize B Chromosome/A Chromosome translocation using B chromosome primers. Control PCR amplicon regions are indicated: BCHR004 for proximal region; BCHR006 for a proximal euchromation region; and BCHR007 for a distal region. The regions for the PCR amplification primers identified from the unique B chromosome sequence are indicated as primers SEQ ID NO:889+890; SEQ ID NO:891+892; and SEQ ID NO:893+894. Abbreviations on schematic of B chromosome are as follows: CK indicates the region of the B chromosome centromere; PH indicates the region of proximal heterochromatin; PE1/PE2 indicates the region of the proximal euchromatin regions; DH1-4 indicates the regions of distal heterochromatin regions; and DE indicates the distal euchromatin region.

DNA was extracted from tissue collected from the tertiary trisomic plants containing the one of the B-A translocation chromosomes (specifically, TB-10L7, TB-10L37, TB-10L3, TB-10L30, TB-10L19, TB-10L26, and TB-10L36); or a sample containing a full-length B chromosome (positive control for all probes); or a sample without a B chromosome (negative control); or a sample from a line with a spontaneously truncated B chromosome. The DNA was used for PCR amplification using PCR amplicon regions BCHR004 for proximal centromere region; BCHR006 for a euchromation region; and BCHR007 for a distal heterochromatin region; and the PCR amplification primer pairs identified from the unique B chromosome sequence (SEQ ID NO:889+890; SEQ ID NO:891+892; and SEQ ID NO:893+894). Results for the presence or absence of a PCR amplicon are presented in Table 3. These results are illustrated in FIG. 2, where the regions of the B chromosome mapped by the probes are indicated by brackets. For example, probe BCHR0004 was mapped to the proximal/centromere region of the B chromosome; probe BCHR0006 was mapped to the proximal euchromatin 2 (PE2) and DH1 region; probe BCHR0007 was mapped to the distal (DH3 and DH4) region; the PCR primer pair amplicon SEQ ID NO:889+890 mapped to the proximal euchromatin 2 (PE2) region; and both PCR primer pair amplicons SEQ ID NO:891+892 and SEQ ID NO:894+894 mapped to the proximal euchromatin 2 (PE2) and DH1 region. These results demonstrate that the unique B chromosome sequences presented as SEQ ID NOs:10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888 are useful for developing PCR primer amplicons useful for B chromosome mapping, and B chromosome unique probe development. The B chromosome unique PCR amplicons and probes have utility in applications of Southern analysis and Northern analysis, as well as other molecular biology and sequence related protocols.

TABLE 3

Result of B-A Translocation mapping.

| B-A translocation source | Control probe BCHR004 | Control probe BCHR006 | Control probe BCHR007 | Primers 889 + 890 | Primers 891 + 892 | Primers 893 + 894 |
|---|---|---|---|---|---|---|
| Full-length B chrom | + | + | + | + | + | + |
| 10L7 | + | − | − | − | − | − |
| 10L37 | + | − | − | − | − | − |
| 10L3 | + | − | − | − | + | + |
| 10L30 | + | + | − | + | + | + |
| 10L19 | + | + | − | + | + | + |
| 10L26 | + | + | − | + | + | + |
| 10L36 | + | + | + | + | + | + |
| spontaneous truncated B | + | + | − | + | + | + |
| No B chrom | − | − | − | − | − | − |

(+) indicates PCR amplicon present,
(−) indicates no PCR amplicon

Example 5: B Chromosome Transgene Insertion

Transformation of transgenes into corn germplasm containing B chromosomes was done to evaluate methods of detecting transgene insertion into corn B chromosome. Two transgene transformation vectors (transformation vector A and transformation vector B) conferring glyphosate tolerance were transformed into corn immature embryos using *Agrobacterium tumefaciens* to produce transgenic plantlets according to methods known to those of skill in the art. The F1 immature embryos used with transformation vector A were derived from a cross of parental germplasm of B73+B chromosomes (range from 6 to 15 B chromosomes) (female) X LH244 (male). The F1 immature embryos used with transformation vector B were derived from a cross of parental germplasm of LH244 (female) X B73+B chromosome (range from 4 to 16 B chromosomes) (male). Following transformation, glyphosate was used to select for progeny containing the transgenes. At the step of transferring the plantlets to soil, root tip samples were taken for FISH analysis. The FISH probes were designed to the transgenes randomly integrated into the corn genome during transformation, and FISH was done essentially as described by Kato et al. (2011), including a DAPI counterstain. From this analysis, no B chromosome insertions were identified with transformation vector A. FISH analysis of root tip tissue from plantlets generated with transformation vector B identified about 10 events of random transgene insertion into B chromosome. Leaf samples were taken from the plants identified by the FISH analysis as having confirmed B chromosome transgene insertion and DNA was prepared. The DNA was used with inverse PCR (Hui, et al. (1998) Cell Mol Life Sci. 54:1403-1422; Tonooka and Fujishima (2009) Appl Microbiol Biotechnol 85:37-43.) to identify flank sequences of the transgene insert. Of the 10 events, 5 had a single copy of the transgene inserted into the B chromosome, and left and right flank sequence was obtained (Table 4). The flank sequence was used to map the transgene insertion site to the B chromosome sequence, thus confirming the FISH analysis.

The unique B chromosome sequences presented as SEQ ID NOs:10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888 are used to select specific target sites for genome modification, to select specific target sites for transgene integration, and to facilitate B chromosome transgene flank identification. Additionally, inclusion of the unique B chromosome sequences presented as SEQ ID NOs:10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888 in genome sequence analysis is used to improve specificity (and thus reducing off-target effects) of target site selection of both A chromosome and B chromosome genome modification.

TABLE 4

B chromosome transgene flank SEQ ID NO

| | SEQ ID NO | |
|---|---|---|
| Event # | Left Flank | Right Flank |
| event 1 | 901 | 902 |
| event 2 | 903 | 904 |
| event 3 | 905 | 906 |
| event 4 | 907 | 908 |
| event 5 | 909 | 910 |

Example 6: B Chromosome Marker Development

The B chromosome sequences identified herein are used for B chromosome marker development, essentially as described in US20060141495, which is incorporated by reference in its entirety herein. Identification of SNP and Indel polymorphisms is accomplished by comparing alignments of sequences of contigs and singletons from at least two separate maize lines. Genomic libraries from multiple maize lines containing B chromosomes are made by isolating genomic DNA from different the maize lines by standard methods known in the art. For genomic libraries, genomic DNA is digested with a restriction endonuclease enzyme (for example, PstI), the digested DNA is size fractionated over 1% agarose gel, and recovered DNA fragments are ligated in a plasmid vector for sequencing by standard molecular biology techniques as described in Green and Sambrook (2012). All sequences are assembled to identify non redundant sequences as described in Example 1 and Example 2. Sequence differences from multiple clones on assembled contigs are identified as single or multiple nucleotide polymorphisms. The B chromosome sequence from multiple maize lines is assembled to into loci having one or more polymorphisms, i.e. SNPs and/or Indels. Candidate polymorphisms are qualified by the following parameters:

(a) The minimum length of a contig or singleton for a consensus alignment is 200 bases.

(b) The percentage identity of observed bases in a region of 15 bases on each side of a candidate SNP, is at least 75%.

(c) The minimum sequence reads in a given contig is 4.

Once regions of polymorphism are identified, Taqman® probes are designed to detect the specific genotype in a corn DNA sample. Such probes can be designed and provided by Applied Biosystems for their proprietary Taqman (Registered trademark) assay (Applied Biosystems, Foster City, Calif.). To confirm that an assay produces accurate results, each new assay is performed on a number of replicates of samples of known genotypic identity representing each of the three possible genotypes, e.g., two homozygous alleles and a heterozygous sample. To be a valid and useful assay, clearly separable clusters of data points, such that one of the three genotypes can be assigned for at least 90% of the data points, and the assignment is observed to be correct for at least 98% of the data points. Subsequent to this validation step, the assay is applied to progeny of a cross between two highly inbred individuals to obtain segregation data, which are then used to calculate a genetic map position for the polymorphic locus. The SNP analysis is also used to aid selection of B chromosome target sites for site-directed genome modification, as detailed in Example 3.

SEQUENCE LISTING

The patent contains a lengthy sequence listing. A copy of the sequence listing is available in electronic form from the USPTO web site (https://seqdata.uspto.gov/?pageRequest=docDetail&DocID=US11732269B2). An electronic copy of the sequence listing will also be available from the USPTO upon request and payment of the fee set forth in 37 CFR 1.19(b)(3).

What is claimed is:

1. A recombinant maize B chromosome comprising at least one transgenic DNA of interest, wherein said at least one transgenic DNA of interest is adjacent to a left flank sequence on one side and a right flank sequence on the other side, and wherein at least one of said left and right flank sequences comprises a nucleic acid sequence having at least 90% sequence identity to at least 0.25 kb of SEQ ID NO: 881, and wherein the at least one transgenic DNA of interest encodes a peptide or an RNAi construct.

2. The recombinant maize B chromosome of claim 1, wherein the transgenic DNA of interest is inserted at a double-strand break generated by one or more site-specific genome modification enzymes.

3. The recombinant maize B chromosome of claim 2, wherein the one or more site-specific genome modification enzyme is selected from an endonuclease, a recombinase, a transposase, a helicase or any combination thereof.

4. The recombinant maize B chromosome of claim 2, wherein the one or more site-specific genome modification enzyme is:
   (a) an endonuclease selected from the group consisting of a meganuclease, a zinc finger nuclease, a transcription activator-like effector nuclease (TALEN), an Argonaute, a DNA-guided recombinase, a DNA-guided endonuclease, an RNA-guided recombinase, an RNA-guided endonuclease, a type I CRISPR-Cas system, type II CRISPR-Cas system and a type III CRISPR-Cas system;
   (b) an endonuclease selected from the group consisting of Cpf1, Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4 nuclease;
   (c) a dCas9-recombinase fusion protein; or
   (d) a tyrosine recombinase, a serine recombinase, a Cre recombinase, a Flp recombinase, a Tnp1 recombinase, a PhiC31 integrase, an R4 integrase, or a TP-901 integrase.

5. The recombinant maize B chromosome of claim 1, wherein the transgenic DNA of interest comprises one or more gene expression cassettes, wherein the gene expression cassettes are selected from the group comprising: an insecticidal resistance gene expression cassette, herbicide tolerance gene expression cassette, nitrogen use efficiency gene expression cassette, a water use efficiency gene expression cassette, a nutritional quality gene expression cassette, a DNA binding gene expression cassette, a selectable marker gene expression cassette, an RNAi construct expression cassette, a site-specific genome modification enzyme gene expression cassette, or an expression cassette encoding one or more of a CRISPR associate protein, a tracr RNA and a guide RNA.

6. A maize plant, maize plant part, or maize plant cell comprising a recombinant maize B chromosome of claim 1.

7. A method of making a transgenic maize cell comprising at least one recombinant maize B chromosome comprising at least one DNA of interest, the method comprising:
   (i) selecting at least one target B chromosome genomic locus, wherein said at least one target B chromosome genomic locus has at least 95% sequence identity to the full length of a sequence selected from the group consisting of SEQ ID NOs: 10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888;

(ii) selecting a site-specific genome modification enzyme that specifically cleaves a sequence within said at least one target B chromosome genomic locus;

(iii) introducing the site-specific genome modification enzyme into the maize cell, wherein said site-specific genomic modification enzyme cleaves the sequence within said at least one target B chromosome genomic locus;

(iv) introducing the at least one DNA of interest into the maize cell, wherein the at least one DNA of interest encodes a peptide or an RNAi construct;

(v) inserting the at least one DNA of interest into the cleaved sequence within the at least one target B chromosome genomic locus; and (vi) selecting a transgenic maize cell comprising at least one recombinant maize B chromosome comprising the at least one DNA of interest, wherein the at least one DNA of interest is inserted into the sequence cleaved by the site-specific genome modification enzyme.

8. The method of claim 7, wherein the insertion of the at least one DNA of interest into the sequence cleaved by the site-specific genome modification enzyme is mediated by homology directed repair.

9. The method of claim 7, wherein the insertion of the at least one DNA of interest into the sequence cleaved by the site-specific genome modification enzyme is mediated by non-homologous end joining.

10. The method of claim 7, wherein at least two DNAs of interest are inserted into the same B chromosome, and wherein the at least two DNAs of interest each comprise between 1,000 and 5,000 nucleotides.

11. The method of claim 10, wherein the at least two DNAs of interest are inserted into at least two target B chromosome genomic loci, wherein said at least two target B chromosome genomic loci are genetically linked but physically separate.

12. The method of claim 11, wherein each of the at least two target B chromosome genomic loci has at least 95% sequence identity to a sequence selected from the group consisting of SEQ ID NOs: 10-13, 16, 19, 21, 22, 24, 25, 32, 34, 38, 40-45, 17-49, 55, 56, 60, 62, 64, 65, 68, 70, 72, 73, 75-79, 81, 83-86, 88-92, 94, 95, 98, 100, 102, 103, 107, 108, 110-112, 114, 116-118, 121, 123, 124, 126, 129-133, 135, 137, 138, 140-150, 154-159, 162-166, 168, 171-180, 183-197, 200-212, 214, 215, 217, 218, 220, 222-225, 228-232, 234-236, 238-241, 243, 244, 247, 249, 251, 253, 254, 256-258, 260-266, 269, 270, 273, 275-279, 281-295, 299, 301, 302, 304-316, 318-320, 322, 323, 325, 327-329, 331-335, 338-344, 346, 347, 349-354, 357-360, 363, 365, 366-373, 375-379, 381, 383, 384, 386-388, 391, 392, 395-398, 400-404, 406-412, 415, 416, 418-420, 422, 423, 428-433, 435-441, 443-446, 448-450, 452, 456-459, 461-464, 466-475, 478, 479, 481-484, 486, 487, 490-495, 497-499, 501-503, 505-508, 510-513, 517-520, 524, 525, 527-529, 531-543, 545-547, 549-554, 556-560, 563-577, 579-584, 586-593, 595, 596, 598-609, 611-614, 616-619, 621-624, 626, 627, 629-636, 638-640, 643-652, 655, 657-661, 663, 664, 666-668, 670-674, 676-680, 683-688, 690-701, 703, 705-708, 711-717, 719-729, 731-734, 736-738, 740, 741, 743-748, 750, 752-764, 766, 767, 770, 771, 773, 774, 776-785, 787-791, and 793-888.

13. The method of claim 7, wherein at least two DNAs of interest are inserted into different B chromosomes.

14. The method of claim 7, wherein the site-specific genome modification enzyme is selected from an endonuclease, a recombinase, a transposase, a helicase or any combination thereof.

15. The method of claim 14, wherein the site-specific genome modification enzyme is:

(a) an endonuclease selected from a meganuclease, a zinc finger nuclease, a transcription activator-like effector nuclease, an Argonaute, a DNA-guided recombinase, a DNA-guided endonuclease, an RNA-guided recombinase, an RNA-guided endonuclease, a type I CRISPR-Cas system, type II CRISPR-Cas system and a type III CRISPR-Cas system;

(b) an endonuclease selected from the group comprising Cpf1, Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4 nuclease;

(c) a dCas9-recombinase fusion protein; or (d) a tyrosine recombinase, a serine recombinase, a Cre recombinase, a Flp recombinase, a Tnp1 recombinase, a PhiC31 integrase, an R4 integrase, or a TP-901 integrase.

16. The method of claim 7, wherein the at least one DNA of interest comprises one or more gene expression cassettes, wherein the gene expression cassettes are selected from the group comprising: an insecticidal resistance gene expression cassette, herbicide tolerance gene expression cassette, nitrogen use efficiency gene expression cassette, a water use efficiency gene expression cassette, a nutritional quality gene expression cassette, a DNA binding gene expression cassette, a selectable marker gene expression cassette, an RNAi construct expression cassette, a site-specific genome modification enzyme gene expression cassette, or an expression cassette encoding one or more of a CRISPR associate protein, a tracr RNA and a guide RNA.

* * * * *